（12） United States Patent
Kamatani et al.

(10) Patent No.: US 11,793,064 B2
(45) Date of Patent: *Oct. 17, 2023

(54) ORGANIC METAL COMPLEX, AND ORGANIC LIGHT EMITTING DEVICE AND DISPLAY APPARATUS USING THE SAME

(71) Applicant: SAMSUNG ELECTRONICS CO., LTD., Suwon-si (KR)

(72) Inventors: Jun Kamatani, Tokyo (JP); Masashi Hashimoto, Tokyo (JP); Satoshi Igawa, Fujisawa (JP); Shinjiro Okada, Kamakura (JP)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 45 days.

This patent is subject to a terminal disclaimer.

(21) Appl. No.: 16/859,356

(22) Filed: Apr. 27, 2020

(65) Prior Publication Data

US 2020/0259106 A1    Aug. 13, 2020

Related U.S. Application Data

(63) Continuation of application No. 16/524,494, filed on Jul. 29, 2019, which is a continuation of application
(Continued)

(30) Foreign Application Priority Data

Nov. 8, 2007   (JP) ................................ 2007-290548

(51) Int. Cl.
*H10K 85/30*    (2023.01)
*C07C 17/14*    (2006.01)
(Continued)

(52) U.S. Cl.
CPC .......... *H10K 85/342* (2023.02); *C07C 17/14* (2013.01); *C07C 45/00* (2013.01);
(Continued)

(58) Field of Classification Search
CPC .................................................. H01L 51/0085
See application file for complete search history.

(56) References Cited

U.S. PATENT DOCUMENTS 6,097,147 A    8/2000  Baldo et al.
6,812,497 B2   11/2004 Kamarani et al.
(Continued)

FOREIGN PATENT DOCUMENTS

JP    2001-247859 A    9/2001
JP    2005-298483 A    10/2005
(Continued)

OTHER PUBLICATIONS

U.S. Appl. No. 60/889,719, filed Feb. 13, 2007.
(Continued)

*Primary Examiner* — William D Young
(74) *Attorney, Agent, or Firm* — CANTOR COLBURN LLP

(57) ABSTRACT

Provided is an organic metal complex having a structure represented by the following general formula (1):

$$ML_mL'_n \qquad (1)$$

where: M represents a metal atom selected from Ir, Pt, Rh, Os, and Zn; L and L', which are different from each other, each represent a bidentate ligand; m represents an integer of 1 to 3 and n represents an integer of 0 to 2, provided that m+n is 3; a partial structure $ML_m$ represents a structure represented by the following general formula (2):

(Continued)

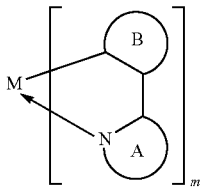

(2)

and a partial structure $ML'_n$ represents a structure including a monovalent bidentate ligand.

16 Claims, 4 Drawing Sheets

Related U.S. Application Data

No. 16/045,842, filed on Jul. 26, 2018, now Pat. No. 10,367,156, which is a continuation of application No. 15/374,364, filed on Dec. 9, 2016, now Pat. No. 10,069,089, which is a continuation of application No. 12/682,628, filed as application No. PCT/JP2008/070633 on Nov. 6, 2008, now Pat. No. 9,554,442.

(51) Int. Cl.
| | | |
|---|---|---|
| C07C 45/00 | (2006.01) | |
| C07F 15/00 | (2006.01) | |
| C09K 11/06 | (2006.01) | |
| H10K 85/10 | (2023.01) | |
| H10K 85/60 | (2023.01) | |
| H05B 33/14 | (2006.01) | |
| C09D 11/50 | (2014.01) | |
| C09K 11/02 | (2006.01) | |
| H10K 50/11 | (2023.01) | |
| H10K 71/00 | (2023.01) | |
| H10K 101/10 | (2023.01) | |
| G09G 3/3233 | (2016.01) | |

(52) U.S. Cl.
CPC .......... *C07F 15/0033* (2013.01); *C09D 11/50* (2013.01); *C09K 11/02* (2013.01); *C09K 11/06* (2013.01); *H05B 33/14* (2013.01); *H10K 85/10* (2023.02); *H10K 85/633* (2023.02); *H10K 85/6572* (2023.02); *C09K 2211/10* (2013.01); *C09K 2211/1011* (2013.01); *C09K 2211/1029* (2013.01); *C09K 2211/185* (2013.01); *G09G 3/3233* (2013.01); *H10K 50/11* (2023.02); *H10K 71/00* (2023.02); *H10K 85/626* (2023.02); *H10K 2101/10* (2023.02)

(56) References Cited

U.S. PATENT DOCUMENTS

| 6,821,645 | B2* | 11/2004 | Igarashi | ............ | C07F 15/0033 |
| | | | | | 428/917 |
| 6,824,894 | B2 | 11/2004 | Takiguchi et al. | | |
| 6,830,828 | B2 | 12/2004 | Thompson et al. | | |
| 6,902,830 | B2 | 6/2005 | Thompson et al. | | |
| 7,001,536 | B2 | 2/2006 | Thompson et al. | | |
| 7,108,924 | B2 | 9/2006 | Kamatani et al. | | |
| 7,238,435 | B2 | 7/2007 | Kamatani et al. | | |
| 7,238,437 | B2 | 7/2007 | Igarashi et al. | | |
| 7,279,233 | B2 | 10/2007 | Tsuboyama et al. | | |
| 7,291,406 | B2 | 11/2007 | Thompson et al. | | |
| 7,361,414 | B2 | 4/2008 | Tsuboyama et al. | | |
| 7,388,327 | B2 | 6/2008 | Kishino et al. | | |
| 7,413,818 | B2 | 8/2008 | Tsuboyama et al. | | |
| 7,459,559 | B2 | 12/2008 | Tsuboyama et al. | | |
| 7,537,844 | B2 | 5/2009 | Thompson et al. | | |
| 7,687,154 | B2 | 3/2010 | Iwawaki et al. | | |
| 9,554,442 | B2 | 1/2017 | Kamatani et al. | | |
| 2003/0068526 | A1 | 4/2003 | Kamatani et al. | | |
| 2003/0072964 | A1 | 4/2003 | Kwong et al. | | |
| 2004/0169622 | A1 | 9/2004 | Matsuura et al. | | |
| 2007/0072001 | A1 | 3/2007 | Tsuboyama et al. | | |
| 2007/0190236 | A1 | 8/2007 | Murata et al. | | |
| 2007/0228940 | A1 | 10/2007 | Hashimoto et al. | | |
| 2007/0231600 | A1 | 10/2007 | Kamatani et al. | | |
| 2007/0231602 | A1 | 10/2007 | Igarashi et al. | | |
| 2007/0232803 | A1 | 10/2007 | Kamatani et al. | | |
| 2007/0259207 | A1 | 11/2007 | Hashimoto et al. | | |
| 2008/0131730 | A1 | 6/2008 | Takiguchi et al. | | |
| 2008/0203908 | A1* | 8/2008 | Hasegawa | ........... | H01L 51/5265 |
| | | | | | 313/504 |
| 2008/0210930 | A1 | 9/2008 | Kamatani et al. | | |
| 2008/0269491 | A1* | 10/2008 | Jabbour | ............. | C07F 15/0033 |
| | | | | | 546/4 |
| 2009/0039776 | A1 | 2/2009 | Yamada et al. | | |
| 2009/0048415 | A1 | 2/2009 | Buesing et al. | | |
| 2009/0091252 | A1 | 4/2009 | Kosuge et al. | | |
| 2009/0209760 | A1 | 8/2009 | Thompson et al. | | |
| 2010/0219407 | A1* | 9/2010 | Kamatani | ............. | H01L 51/006 |
| | | | | | 257/40 |
| 2010/0289406 | A1 | 11/2010 | Ma et al. | | |

FOREIGN PATENT DOCUMENTS

| JP | 2005-344124 A | 12/2005 |
| WO | 02/44189 A1 | 6/2002 |

OTHER PUBLICATIONS

European Office Action received in corresponding EP application No. 08846931.7 dated Nov. 25, 2014—4 pages.
Chen et al., "Recent Developments in Molecular Organic Electroluminescent Materials," Macromol. Symp., vol. 125, pp. 1-48 (1997).
Korivi, et al., "Highly Efficient Synthesis of Isoquinolines via Nickel-Catalyzed Annulation of 2-Iodobenzaldimines with Alkynes: Evidence for Dual Pathways of Alkyne Insertion," Org. Chem. Lett., vol. 7, No. 23, pp. 5179-5182 (2005).
Wiley, et al., "Substituted 4,7-Penanthrolines and Benzo(f)quinolines as Scintillation Solutes," J. Org. Chem., vol. 23, pp. 268-271 (1958).
Roesch, et al., "Synthesis of Isoquinolines and Pyridines by the Palladium-Catalyzed Iminoannulation of Internal Alkynes," J. Org. Chem., vol. 66, pp. 8042-8051 (2001).
Eloy, et al., "Sur une methode nouvelle de synthese des aza-2 phenanthrenes (benzo[t]isoquinoleines) (Note de laboratoire)," Chimica Therapeutica, The European Journal of Medicinal Chemistry, vol. 6, No. 1, pp. 49-49 (1971).
Baldo, et al., "Very high-efficiency green organic light-emitting devices based on electrophosphorescence," Appl. Phys. Lett., vol. 75, No. 1, pp. 4-6 (1999).
International Preliminary Report on Patentability dated May 20, 2010, issued in corresponding International Application No. PCT/JP2008/070633—6 pages.
O'Brien, et al., "Improved energy transfer in electrophosphorescent devices," Applied Physics Letters, vol. 74, No. 3, pp. 442-444 (1999).

* cited by examiner

ORGANIC METAL COMPLEX, AND ORGANIC LIGHT EMITTING DEVICE AND DISPLAY APPARATUS USING THE SAME

CROSS REFERENCE TO RELATED APPLICATIONS

This application is a continuation application of U.S. patent application Ser. No. 16/524,494, filed on Jul. 29, 2019, which is a continuation application of U.S. patent application Ser. No. 16/045,842, filed on Jul. 26, 2018, which is a continuation application of U.S. patent application Ser. No. 15/374,364, filed on Dec. 9, 2016, which is a continuation application of U.S. patent application Ser. No. 12/682,628, filed on Apr. 12, 2010, which claims priority to an International Patent Application No. PCT/JP2008/070633, filed on Nov. 6, 2008, which claims priority to Japanese Patent Application No. 2007-290548, filed Nov. 8, 2007, and all the benefits accruing therefrom under 35 U.S.C. § 119, the disclosure of which is incorporated herein in its entirety by reference.

TECHNICAL FIELD

The present invention relates to an organic metal complex, and an organic light emitting device and a display apparatus using the organic metal complex.

BACKGROUND ART

An organic light emitting device is a device in which a thin film including a fluorescent organic compound is sandwiched between an anode and a cathode. Further, electrons and holes are injected from the respective electrodes to generate exciton of the fluorescent compound, whereby the organic light emitting device emits light when the exciton returns to a ground state.

Recent progress of an organic light emitting device is remarkable, and the characteristics of the device enable a light emitting device with a high luminance at a low applied voltage, a variety of emission wavelengths, high-speed responsiveness, thin and light weight. From this fact, it is suggested that the organic light emitting device have potential to find use in a wide variety of applications.

However, the present situation calls for optical output with even higher luminance or higher conversion efficiency. In addition, many problems still remain to be solved regarding durability against the change over time due to long-term use, deterioration caused by atmospheric gas containing oxygen, moisture, or the like.

Further, when considering application to a full color display or the like, the present art is still insufficient against problems relating to the needs for light emission of a red color with high color purity and high efficiency. On the other hand, an organic light emitting device having, in particular, high color purity, high light emitting efficiency, and high durability, and a material realizing the organic light emitting device have been demanded.

By the way, as a light emitting material which can utilize light emission from a triplet excitation state, an iridium (Ir) complex has been proposed. Examples of the Ir complex to be used as the light emitting material herein include the Ir complexes disclosed in Macromol. Symp. 125, 1-48 (1997), "Improved energy transfer in electrophosphorescent device", D. F. O'Brien, et al., Applied Physics Letters, Vol. 74, No. 3, p. 422 (1999), "Very high-efficiency green organic light-emitting devices based on electrophosphorescence", M. A. Baldo, et al., Applied Physics Letters, Vol. 75, No. 1, p. 4 (1999), Japanese Patent Application Laid-Open No. 2001-247859, and Japanese Patent Application Laid-Open No. 2005-344124.

DISCLOSURE OF THE INVENTION

The present invention is accomplished to solve the above-mentioned problems of the conventional art. That is, an object of the present invention is to provide a novel Ir complex. Further, another object of the present invention is to provide an organic light emitting device having light emission with high efficiency and high luminance, and having durability.

An organic metal complex of the present invention has a structure represented by the following general formula (1):

where: M represents a metal atom selected from Ir, Pt, Rh, Os, and Zn; L and L', which are different from each other, each represent a bidentate ligand; m represents an integer of 1 to 3 and n represents an integer of 0 to 2, provided that m+n is 3; a partial structure $ML_m$ represents a structure represented by the following general formula (2):

where: A represents a structure represented by any one of the following general formulae (3) to (7), which has, as a basic skeleton, one of benzo[f]quinoline, benzo[h]quinoline, benzo[f]isoquinoline, and benzo[h]isoquinoline:

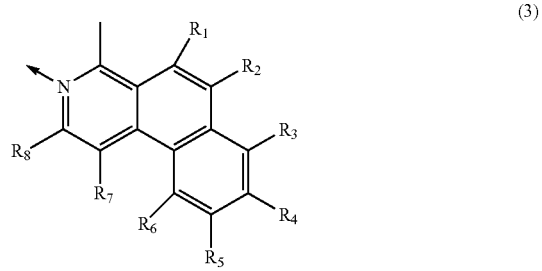

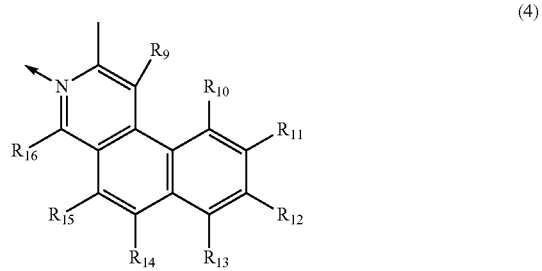

-continued

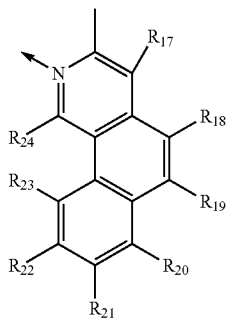

(5)

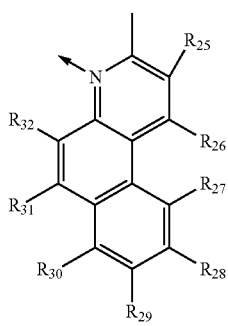

(6)

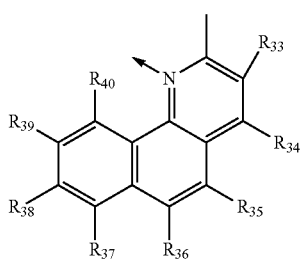

(7)

where $R_1$ to $R_{40}$, which may be identical to or different from each other, each represent a hydrogen atom, a halogen atom, a substituted or unsubstituted alkyl group, an alkoxy group, an aralkyl group, a substituted amino group, a substituted or unsubstituted aryl group, or a substituted or unsubstituted heterocyclic group, and adjacent substituents among $R_1$ to $R_{40}$ may be bonded to form a ring; and B represents a benzene ring which may have a substituent, a fused ring which may have a substituent, a vinyl group which may have a substituent, or a heterocycle which may have a substituent; and a partial structure $ML'_n$ represents a structure including a monovalent bidentate ligand.

According to the present invention, there can be provided the novel Ir complex and the organic light emitting device having light emission with high efficiency and high luminance, and having durability.

BEST MODE FOR CARRYING OUT THE INVENTION

Figure 1:
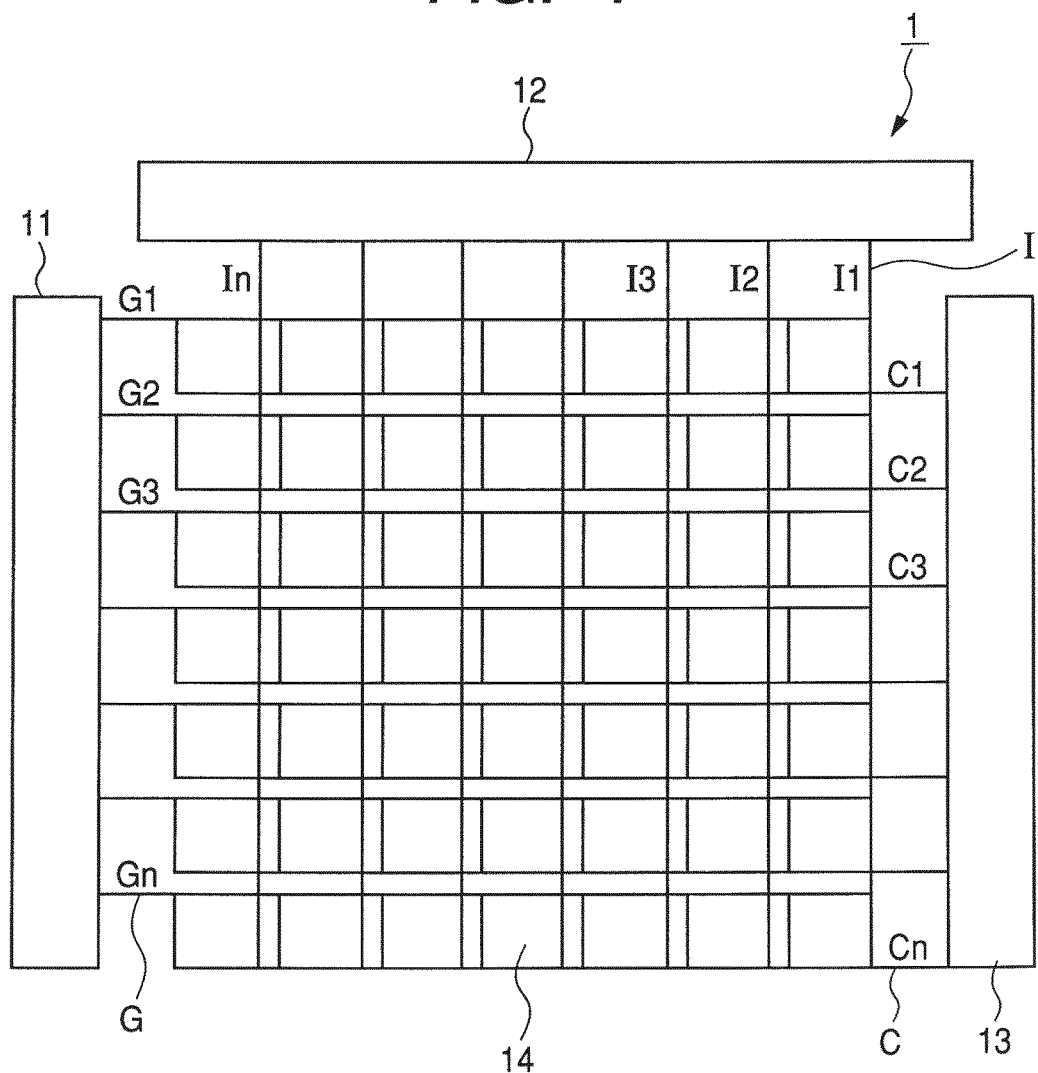
FIG. 1 is a diagram illustrating schematically a configuration example of a display apparatus including an organic light emitting device of the present invention and a driving unit, which is an embodiment of a display apparatus.

An organic metal complex of the present invention is an organic metal complex having a structure represented by the following general formula (1):

$$ML_m L'_n \qquad (1)$$

where: M represents a metal atom selected from Ir, Pt, Rh, Os, and Zn;

$L_m$ and $L'_n$, which are different from each other, each represent a bidentate ligand, and specific structures of L and L' are described below; and m represents an integer of 1 to 3 and n represents an integer of 0 to 2, provided that m+n is 3.

Hereinafter, the specific structure of L is described. A partial structure $ML_m$ of the complex containing L is represented by the following general formula (2):

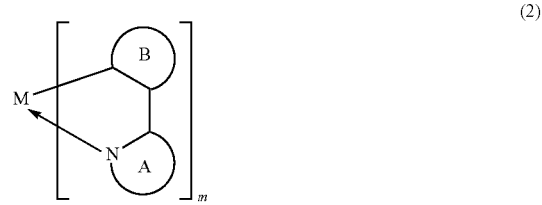

(2)

where A represents a structure represented by any one of the following general formulae (3) to (7), which has, as a basic skeleton, one of benzo[f]quinoline, benzo[h]quinoline, benzo[f]isoquinoline, and benzo[h]isoquinoline:

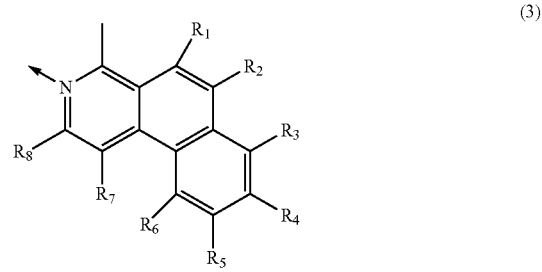

(3)

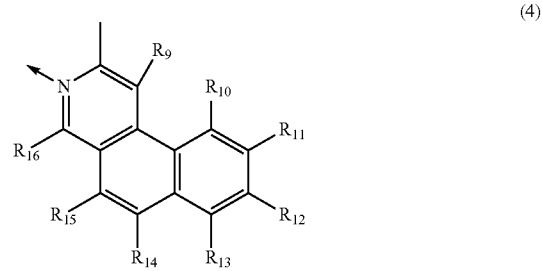

(4)

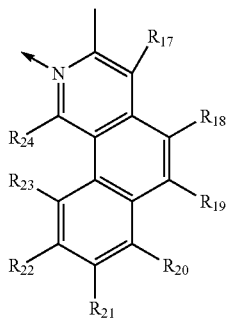
(5)

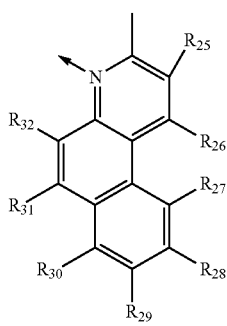
(6)

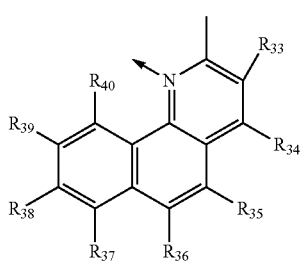
(7)

where $R_1$ to $R_{40}$ each represent a hydrogen atom, a halogen atom, a substituted or unsubstituted alkyl group, an alkoxy group, an aryloxy group, an aralkyl group, a substituted amino group, a substituted or unsubstituted aryl group, or a substituted or unsubstituted heterocyclic group.

Examples of the halogen atom represented by $R_1$ to $R_{40}$ include fluorine, chlorine, bromine, and iodine.

Examples of the alkyl group represented by $R_1$ to $R_{40}$ include, but of course are not limited to, a methyl group, an ethyl group, an n-propyl group, an isopropyl group, an n-butyl group, a t-butyl group, a sec-butyl group, an octyl group, a 1-adamantyl group, and a 2-adamantyl group.

Examples of the alkoxy group represented by $R_1$ to $R_{40}$ include, but of course are not limited to, a methoxy group, an ethoxy group, a propoxy group, a 2-ethyl-octyloxy group, and a benzyloxy group.

Examples of the aryloxy group represented by $R_1$ to $R_{40}$ include, but of course are not limited to, a phenoxy group, a 4-tert-butyl phenoxy group, and a thienyloxy group.

Examples of the aralkyl group represented by $R_1$ to $R_{40}$ include, but of course are not limited to, a benzyl group.

Examples of the substituted amino group represented by $R_1$ to $R_{40}$ include, but of course are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of the aryl group represented by $R_1$ to $R_{40}$ include, but of course are not limited to, a phenyl group, a naphthyl group, an indenyl group, a pyrenyl group, an indacenyl group, an acenaphthenyl group, a phenanthryl group, a fluoranthenyl group, a triphenylenyl group, a chrysenyl group, a naphthacenyl group, a perylenyl group, a biphenyl group, a terphenyl group, and a fluorenyl group.

Examples of the heterocyclic group represented by $R_1$ to $R_{40}$ include, but of course are not limited to, a pyridyl group, an oxazolyl group, an oxadiazolyl group, a thiazolyl group, a thiadiazolyl group, a carbazolyl group, an acridinyl group, and a phenanthrolyl group.

Examples of the substituent that the alkyl group, the aryl group, and the heterocyclic group each may further have include, but of course are not limited to: alkyl groups such as a methyl group, an ethyl group, and a propyl group; aralkyl groups such as a benzyl group; aryl groups such as a phenyl group, a biphenyl group, a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; and halogen atoms such as fluorine, chlorine, bromine, and iodine; and a cyano group.

The substituents represented by $R_1$ to $R_8$, $R_9$ to $R_{16}$, $R_{17}$ to $R_{24}$, $R_{25}$ to $R_{32}$, or $R_{33}$ to $R_{40}$ may each be identical to or different from one another.

In addition, of those substituents represented by $R_1$ to $R_3$, $R_9$ to $R_{16}$, $R_{17}$ to $R_{24}$, $R_{25}$ to $R_{32}$, or $R_{33}$ to $R_{40}$, adjacent substituents may be bonded to form a ring such as a benzene ring, an indene ring, a naphthalene ring, a pyridine ring, a pyrrole ring, or a cyclohexyl ring.

In the formula (2), B represents a benzene ring which may have a substituent, a fused ring which may have a substituent, a vinyl group which may have a substituent, or a heterocycle which may have a substituent.

Examples of the substituent that the benzene ring, fused ring, vinyl group, and heterocycle each may further have include halogen atoms, substituted or unsubstituted alkyl groups, alkoxy groups, aryloxy groups, aralkyl groups, substituted amino groups, substituted or unsubstituted aryl groups, and substituted or unsubstituted heterocyclic groups.

Examples of the halogen atom include fluorine, chlorine, bromine, and iodine.

Examples of the alkyl groups include, but of course are not limited to, a methyl group, an ethyl group, an n-propyl group, an isopropyl group, an n-butyl group, a tert-butyl group, a sec-butyl group, an octyl group, a 1-adamantyl group, and a 2-adamantyl group.

Examples of the alkoxy group include, but of course are not limited to, a methoxy group, an ethoxy group, a propoxy group, a 2-ethyl-octyloxy group, and a benzyloxy group.

Examples of the aryloxy group include, but of course are not limited to, a phenoxy group, a 4-tert-butyl phenoxy group, and a thienyloxy group.

Examples of the aralkyl group include, but of course are not limited to, a benzyl group.

Examples of the substituted amino group include, but of course are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of the aryl group include a phenyl group, a naphthyl group, an indenyl group, a pyrenyl group, an indacenyl group, an acenaphthenyl group, a phenanthryl group, a fluoranthenyl group, a triphenylenyl group, a chrysenyl group, a naphthacenyl group, a perylenyl group, a biphenyl group, a terphenyl group, and a fluorenyl group.

Examples of the heterocyclic group include, but of course are not limited to, a pyridyl group, an oxazolyl group, an oxadiazolyl group, a thiazolyl group, a thiadiazolyl group, a carbazolyl group, an acridinyl group, and a phenanthrolyl group.

Examples of the substituent that the alkyl group, the aryl group, and the heterocyclic group each may further have include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; and halogen atoms such as fluorine, chlorine, bromine, and iodine; and a cyano group.

Hereinafter, the specific structure of L' in the formula (1) is described. A partial structure $ML'_n$ of the complex containing L' is a structure containing monovalent bidentate ligand (L').

Here, specific examples of the monovalent bidentate ligand are not particularly limited, but include ligands each having, as a basic skeleton, acetylacetone, phenylpyridine, picolinic acid, oxalate, or salene.

The organic metal complex of the present invention is preferably the organic metal complex represented by the formula (1) where M represents Ir, the partial structure $ML_m$ represents a structure represented by the following general formula (8) or (9), and the partial structure $ML'_n$ represents a structure represented by any one of the following general formulae (10) to (12).

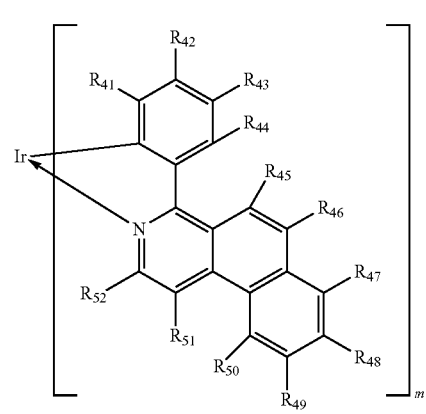

(8)

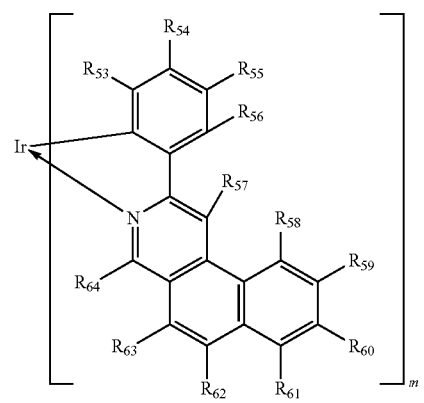

(9)

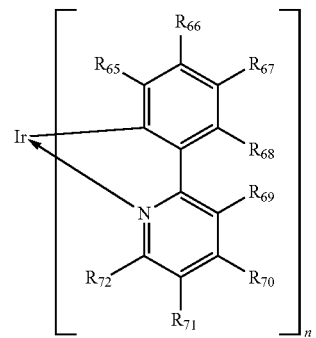

(10)

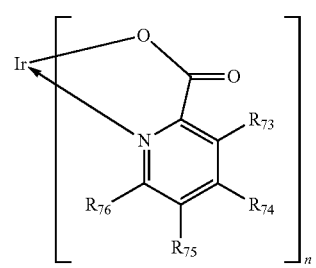

(11)

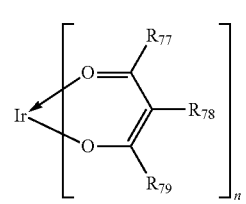

(12)

First, the partial structure $ML_m$ is described. Note that m has the same meaning as m in the formula (1).

In the formulae (8) and (9), $R_{41}$ to $R_{64}$ each represent a hydrogen atom, a halogen atom, a substituted or unsubstituted alkyl group, an alkoxy group, an aralkyl group, an amino group, a substituted or unsubstituted aryl group, or a substituted or unsubstituted heterocyclic group.

Examples of the halogen atom represented by $R_{41}$ to $R_{64}$ include fluorine, chlorine, bromine, and iodine.

Examples of the alkyl group represented by $R_{41}$ to $R_{64}$ include, but of course are not limited to, a methyl group, an ethyl group, an n-propyl group, an isopropyl group, an n-butyl group, a tert-butyl group, a sec-butyl group, an octyl group, a 1-adamantyl group, and a 2-adamantyl group.

Examples of the alkoxy group represented by $R_{41}$ to $R_{64}$ include, but of course are not limited to, a methoxy group, an ethoxy group, a propoxy group, a 2-ethyl-octyloxy group, and a benzyloxy group.

Examples of the aryloxy group represented by $R_{41}$ to $R_{64}$ include, but of course are not limited to, a phenoxy group, a 4-tert-butyl phenoxy group, and a thienyloxy group.

Examples of the aralkyl group represented by $R_{41}$ to $R_{64}$ include, but of course are not limited to, a benzyl group.

Examples of the substituted amino group represented by $R_{41}$ to $R_{64}$ include, but of course are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of the aryl group represented by $R_{41}$ to $R_{64}$ include a phenyl group, a naphthyl group, an indenyl group, a pyrenyl group, an indacenyl group, an acenaphthenyl group, a phenanthryl group, a fluoranthenyl group, a triphenylenyl group, a chrysenyl group, a naphthacenyl group, a perylenyl group, a biphenyl group, a terphenyl group, and a fluorenyl group.

Examples of the heterocyclic group represented by $R_{41}$ to $R_{64}$ include, but of course are not limited to, a pyridyl group, an oxazolyl group, an oxadiazolyl group, a thiazolyl group, a thiadiazolyl group, a carbazolyl group, an acridinyl group, and a phenanthrolyl group.

Examples of the substituent that the alkyl group, the aryl group, and the heterocyclic group each may further have include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, dibenzylamino group, a diphenylamino group, and a ditolylamino group; alkoxyl groups such as a methoxyl group, an ethoxyl group, and a propoxyl group; aryloxyl groups such as a phenoxyl group; and halogen atoms such as fluorine, chlorine, bromine, and iodine; and a cyano group.

The substituents represented by $R_{41}$ to $R_{52}$ or $R_{53}$ to $R_{64}$ may each be identical to or different from one another.

In addition, of those substituents represented by $R_{41}$ to $R_{52}$ or $R_{53}$ to $R_{64}$, adjacent substituents may be bonded to form a ring such as a benzene ring, an indene ring, a naphthalene ring, a pyridine ring, a pyrrole ring, or a cyclohexyl ring.

Next, the partial structure $ML'_n$ is described. Note that n has the same meaning as n in the formula (1).

In the formulae (10) to (12), $R_{65}$ to $R_{79}$ each represent a hydrogen atom, a halogen atom, a substituted or unsubstituted alkyl group, an alkoxy group, an aralkyl group, a substituted amino group, a substituted or unsubstituted aryl group, or a substituted or unsubstituted heterocyclic group.

Examples of the halogen atom represented by $R_{65}$ to $R_{79}$ include fluorine, chlorine, bromine, and iodine.

Examples of the alkyl group represented by $R_{65}$ to $R_{79}$ include, but of course are not limited to, a methyl group, an ethyl group, an n-propyl group, an isopropyl group, an n-butyl group, a tert-butyl group, a sec-butyl group, an octyl group, a 1-adamantyl group, and a 2-adamantyl group.

Examples of the alkoxy group represented by $R_{65}$ to $R_{79}$ include, but of course are not limited to, a methoxy group, an ethoxy group, a propoxy group, a 2-ethyl-octyloxy group, and a benzyloxy group.

Examples of the aryloxy group represented by $R_{65}$ to $R_{79}$ include, but of course are not limited to, a phenoxy group, a 4-tert-butyl phenoxy group, and a thienyloxy group.

Examples of the aralkyl group represented by $R_{65}$ to $R_{79}$ include, but of course are not limited to, a benzyl group.

Examples of the substituted amino group represented by $R_{65}$ to $R_{79}$ include, but of course are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of the aryl group represented by $R_{65}$ to $R_{79}$ include a phenyl group, a naphthyl group, an indenyl group, a pyrenyl group, an indacenyl group, an acenaphthenyl group, a phenanthryl group, a fluoranthenyl group, a triphenylenyl group, a chrysenyl group, a naphthacenyl group, a perylenyl group, a biphenyl group, a terphenyl group, and a fluorenyl group.

Examples of the heterocyclic group represented by $R_{65}$ to $R_{79}$ include, but of course are not limited to, a pyridyl group, an oxazolyl group, an oxadiazolyl group, a thiazolyl group, a thiadiazolyl group, a carbazolyl group, an acridinyl group, and a phenanthrolyl group.

Examples of the substituent that the alkyl group, the aryl group, and the heterocyclic group each may further have include: alkyl groups such as a methyl group, an ethyl group, and a propyl group; an aralkyl group such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; halogen atoms such as fluorine, chlorine, bromine, and iodine; and a cyano group.

The substituents represented by $R_{65}$ to $R_{72}$, $R_{73}$ to $R_{76}$, or $R_{77}$ to $R_{79}$ may each be identical to or different from one another.

In addition, of those substituents represented by $R_{65}$ to $R_{72}$, $R_{73}$ to $R_{76}$, or $R_{77}$ to $R_{79}$, adjacent substituents may be bonded to form a ring such as a benzene ring, an indene ring, a naphthalene ring, a pyridine ring, a pyrrole ring, or a cyclohexyl ring.

Next, the synthesis method for an organic metal complex of the present invention is described. The organic metal complexes represented by the general formulae (1) and (6) to (9) can be synthesized with reference to J. Org. Chem. (2001), Vol. 66, 8042-8051, Org. Lett., Vol. 7, No. 18, 2005, Org. Lett., Vol. 7, No. 23, 2005, Chimica Therapeutica (1971), Vol. 6(1), 48-9, and J. Org. Chem. (1958), Vol. 23268-71.

Specifically, the organic metal complex can be synthesized through the following steps.

(i) Synthesis of an organic compound serving as a ligand
(ii) Synthesis of an organic metal complex Here, the organic compound serving as a ligand can be synthesized by any one of Synthetic Routs 1 to 3, for example.

Synthetic Route 1

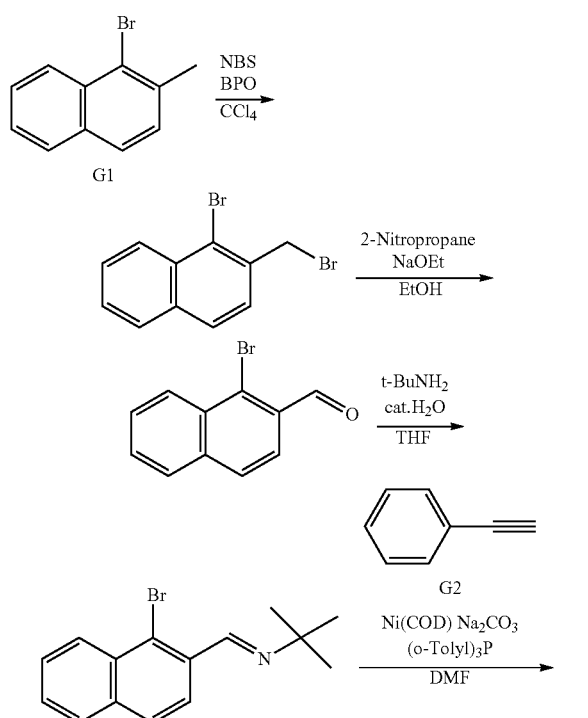

Synthetic Route 2

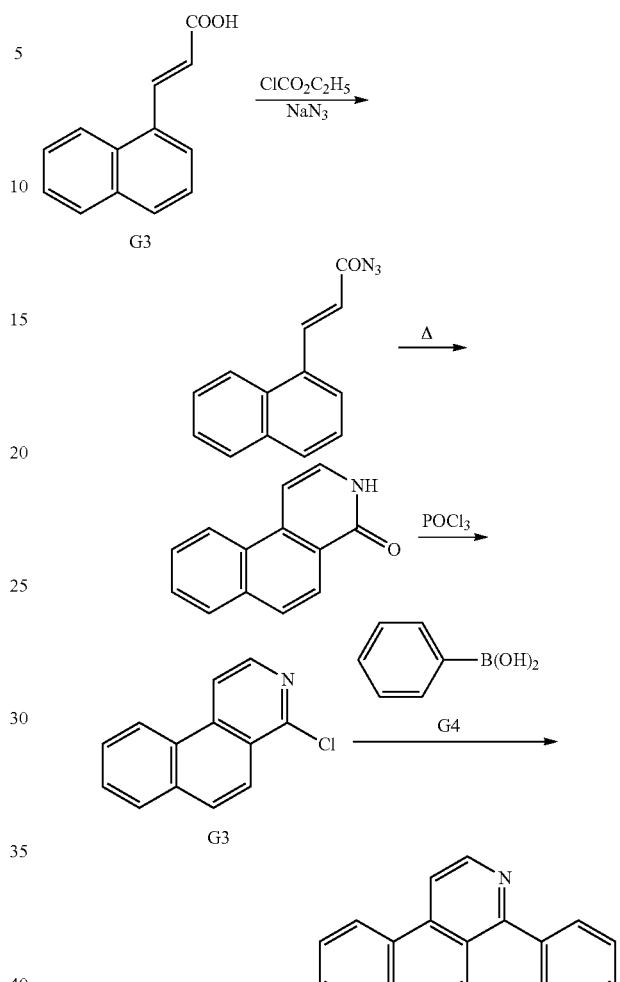

Synthetic Route 3

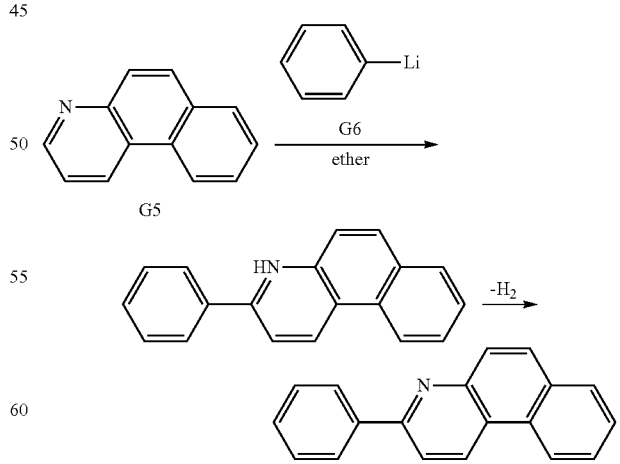

Note that, whichever of Synthetic Routes 1 to 3 is employed, an organic compound as a starting substance is not limited to one of Compounds G1 to G6 represented in Synthetic Routes 1 to 3.

Here, in the case of employing Synthetic Route 1, combinations of a bromo body as a starting substance, an arylacetylene as a starting substance, and a ligand to be synthesized are given in Table 1 below, for example, but the present invention is not limited thereto.
TABLE 1
| | Bromo body | Arylacetylene | Ligand to be synthesized |
|---|---|---|---|
| 1 | 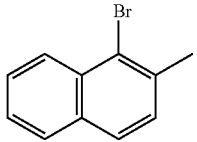 | 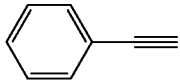 | 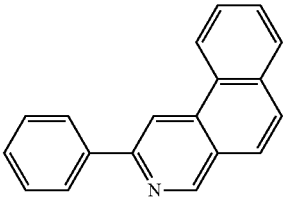 [SMILES: c1ccc(-c2cc3c(ccc4ccccc43)cn2)cc1] |
| 2 | 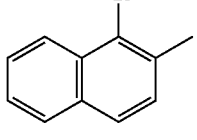 | 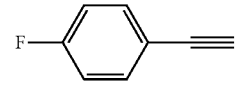 | 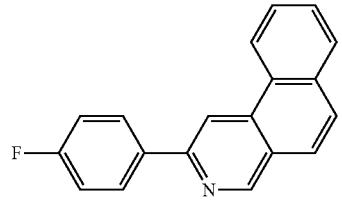 [SMILES: Fc1ccc(-c2cc3c(ccc4ccccc43)cn2)cc1] |
| 3 | 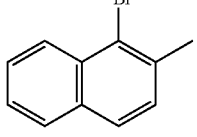 | 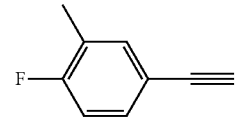 | 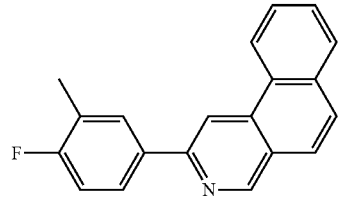 [SMILES: Cc1cc(-c2cc3c(ccc4ccccc43)cn2)ccc1F] |
| 4 | 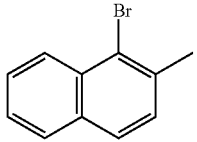 | 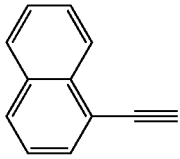 | 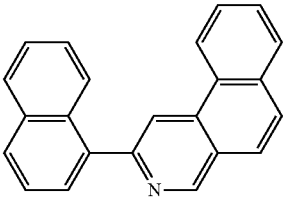 [SMILES: c1ccc2c(-c3cc4c(ccc5ccccc54)cn3)cccc2c1] |
| 5 | 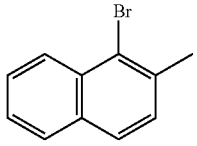 | 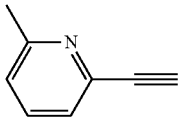 | 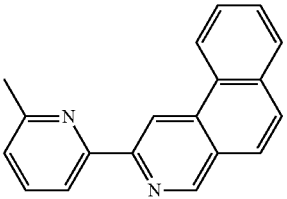 [SMILES: Cc1cccc(-c2cc3c(ccc4ccccc43)cn2)n1] |
| 6 | 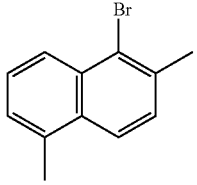 | 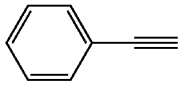 | 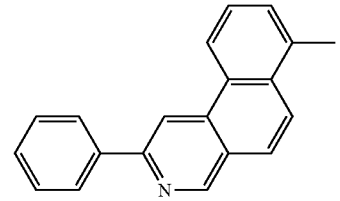 [SMILES: Cc1cccc2c1ccc1cnc(-c3ccccc3)cc12] |

TABLE 1-continued

| | Bromo body | Arylacetylene | Ligand to be synthesized |
|---|---|---|---|
| 7 | 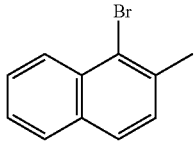 | 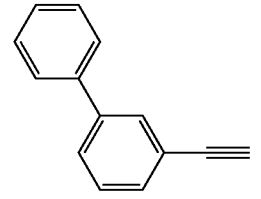 | 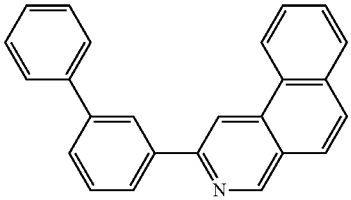 [SMILES: c1ccc(-c2cccc(-c3cc4c(ccc5ccccc54)cn3)c2)cc1] |
| 8 | 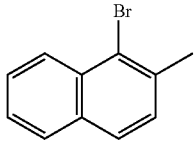 | 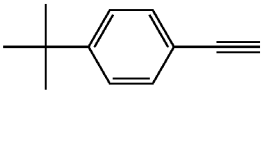 | 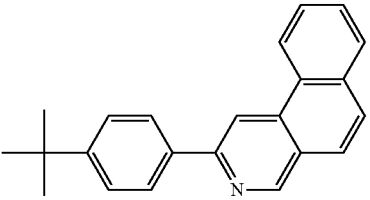 [SMILES: CC(C)(C)c1ccc(-c2cc3c(ccc4ccccc43)cn2)cc1] |

On the other hand, in the case of employing Synthetic Route 2, combinations of a chloro body as a starting substance, a boronic acid or an organic metal compound as a starting substance, and a ligand to be synthesized are given in Table 2 below, for example, but the present invention is not limited thereto.

TABLE 2

| | Chloro body | Boronic acid or organic metal compound | Ligand to be synthsized |
|---|---|---|---|
| 9 | 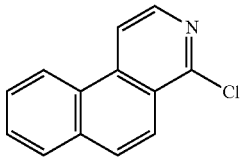 [SMILES: Clc1nccc2c1ccc1ccccc12] | 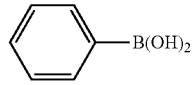 | 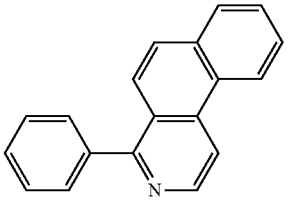 [SMILES: c1ccc(-c2nccc3c2ccc2ccccc23)cc1] |
| 10 | 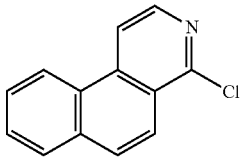 [SMILES: Clc1nccc2c1ccc1ccccc12] | 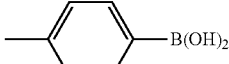 | 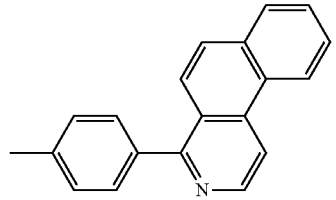 [SMILES: Cc1ccc(-c2nccc3c2ccc2ccccc23)cc1] |
| 11 | 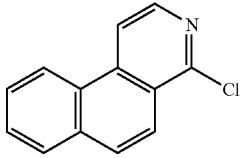 [SMILES: Clc1nccc2c1ccc1ccccc12] | 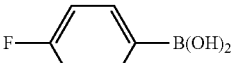 | 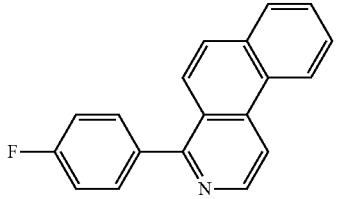 [SMILES: Fc1ccc(-c2nccc3c2ccc2ccccc23)cc1] |
| 12 | 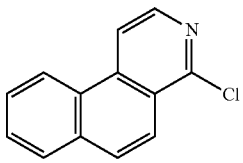 [SMILES: Clc1nccc2c1ccc1ccccc12] | 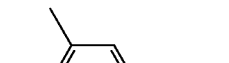 | 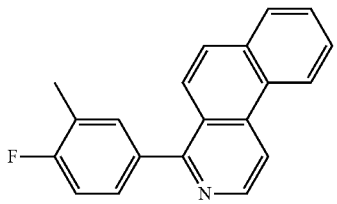 [SMILES: Cc1cc(-c2nccc3c2ccc2ccccc23)ccc1F] |

TABLE 2-continued
| | Chloro body | Boronic acid or organic metal compound | Ligand to be synthsized |
|---|---|---|---|
| 13 | 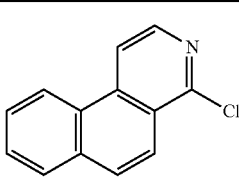 | 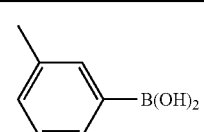 | 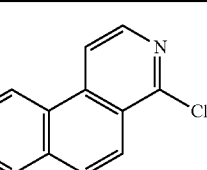 |
| 14 | 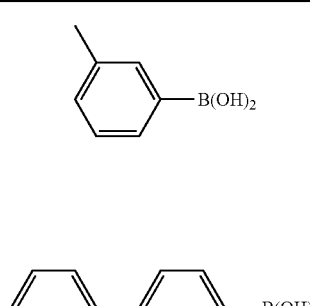 | 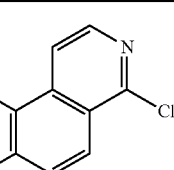 | 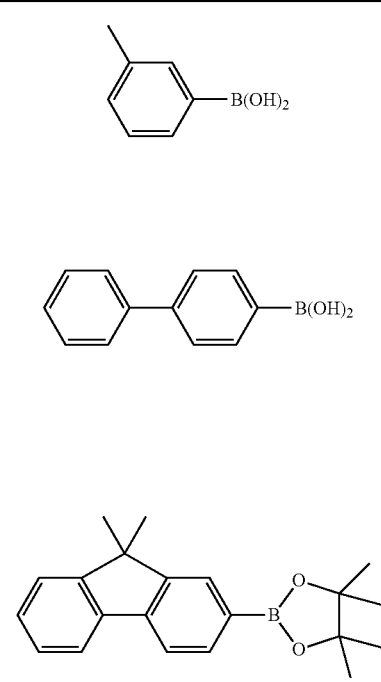 |
| 15 | 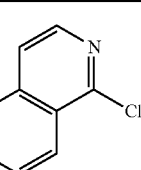 | 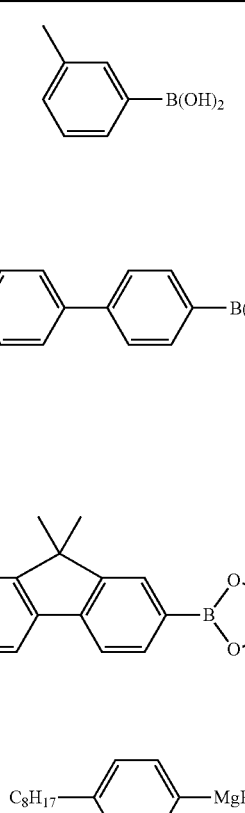 | 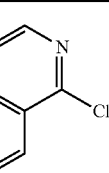 |
| 16 | 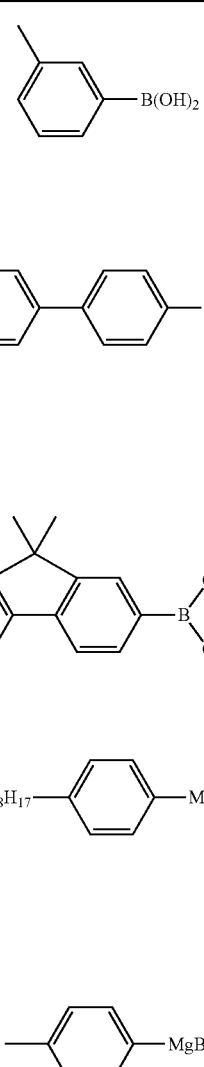 | 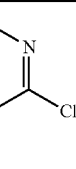 | 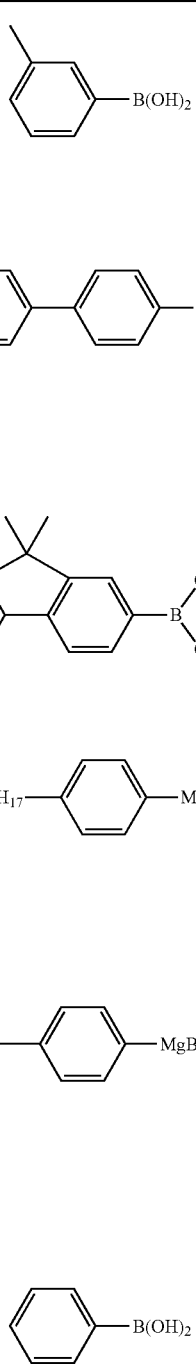 |
| 17 | | | |
| 18 | | | |

TABLE 2-continued

| | Chloro body | Boronic acid or organic metal compound | Ligand to be synthsized |
|---|---|---|---|
| 19 | 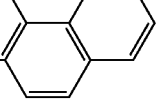 | 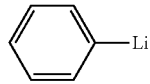 | 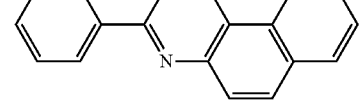 |
| 20 | 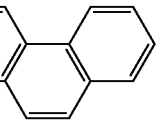 | 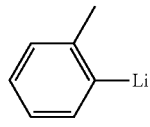 | 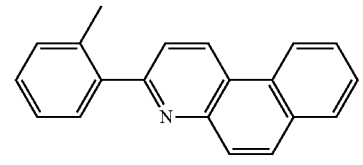 [SMILES: Cc1ccccc1-c1ccc2c(ccc3ccccc32)n1] |

On the other hand, in the case of employing Synthetic Route 3, combinations of a benzoquinoline derivative as a starting substance, a lithium compound as a starting substance, and a ligand to be synthesized are given in Table 3 below, for example, but the present invention is not limited thereto.

TABLE 3

| | Benzoquinoline derivative | Lithium compound | Ligand to besynthesized |
|---|---|---|---|
| 21 | 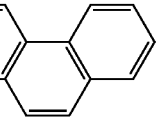 | 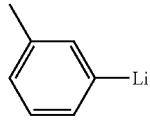 | 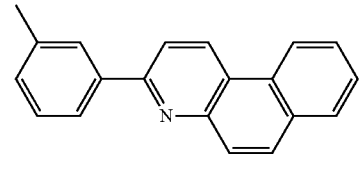 [SMILES: Cc1cccc(-c2ccc3c(ccc4ccccc43)n2)c1] |
| 22 | 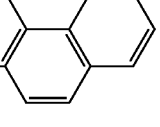 | 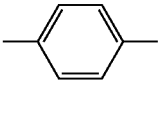 | 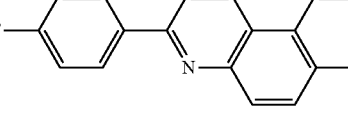 |
| 23 | 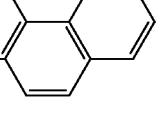 | 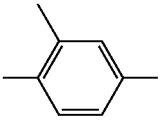 | 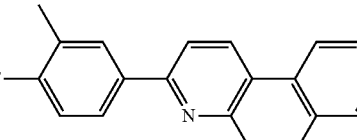 |
| 24 | | | |
| 25 | | | |

TABLE 3-continued

| | Benzoquinoline derivative | Lithium compound | Ligand to be synthesized |
|---|---|---|---|
| 26 | | | |
| 27 | | | |
| 28 | | | |
| 29 | | | |
| 30 | | | |

The various ligands synthesized by Synthetic Routes 1 to 3 are used, whereby the organic metal complex of the present invention can be synthesized by any one of Synthetic Routes 4 to 6.

Synthetic Route 4

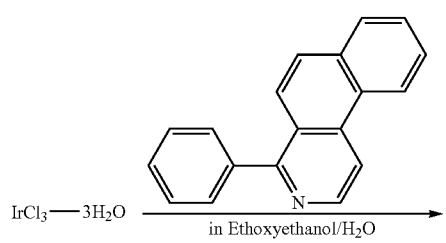

$\text{IrCl}_3\text{—}3\text{H}_2\text{O} \xrightarrow{\text{in Ethoxyethanol/H}_2\text{O}}$

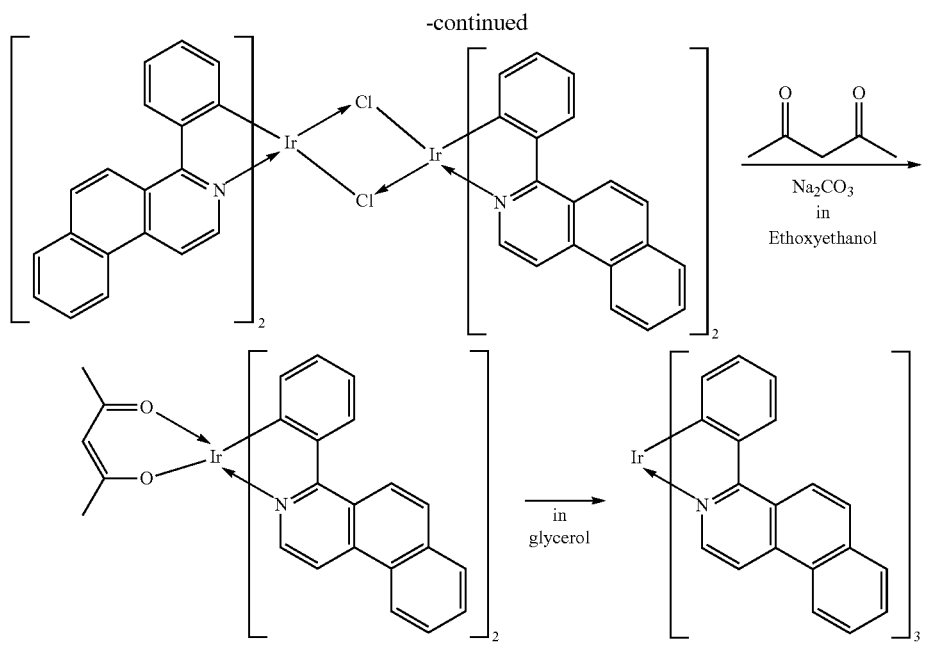

Synthetic Route 5

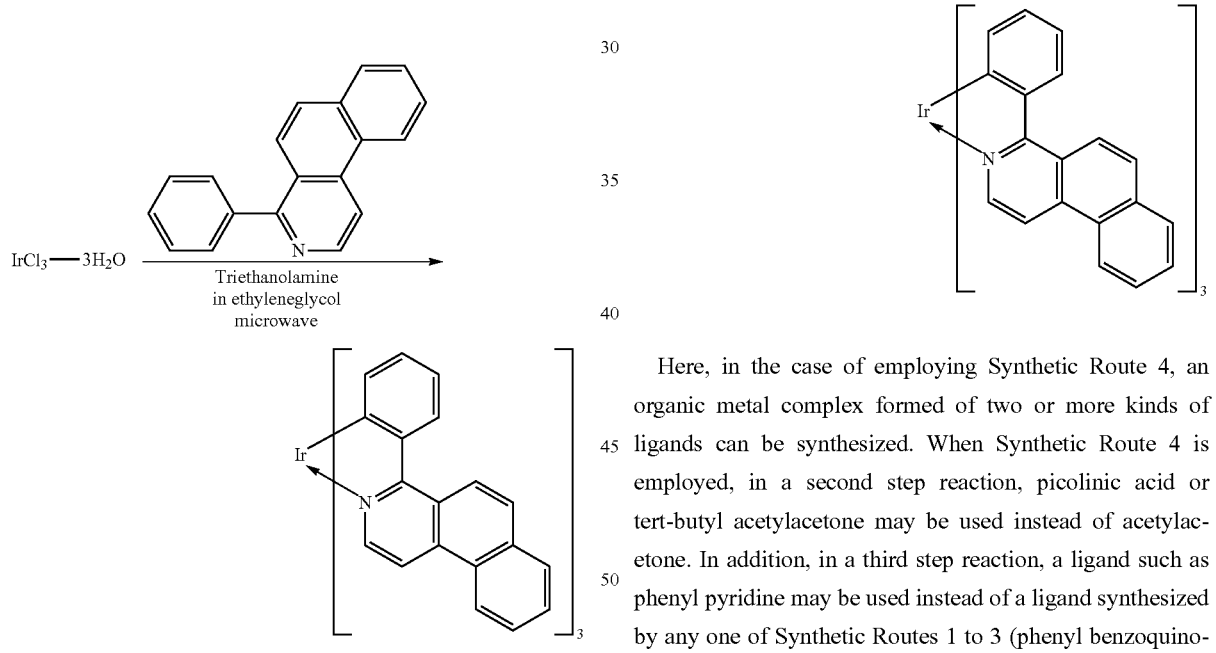

Synthetic Route 6

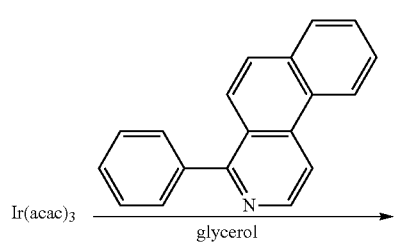

Here, in the case of employing Synthetic Route 4, an organic metal complex formed of two or more kinds of ligands can be synthesized. When Synthetic Route 4 is employed, in a second step reaction, picolinic acid or tert-butyl acetylacetone may be used instead of acetylacetone. In addition, in a third step reaction, a ligand such as phenyl pyridine may be used instead of a ligand synthesized by any one of Synthetic Routes 1 to 3 (phenyl benzoquinoline, phenyl benzoisoquinoline).

As described above, the organic metal complex of the present invention includes one kind or two kinds of bidentate ligands and a metal atom such as Ir. In addition, the bidentate ligand has, as a basic skeleton, a heterocyclic skeleton containing a nitrogen atom which forms a coordinate bond with the metal atom. Specifically, as a basic skeleton, the bidentate ligand has, as a basic skeleton, one of benzo[f]quinoline, benzo[h]quinoline, benzo[f]isoquinoline, and benzo[h]isoquinoline, which are shown below.

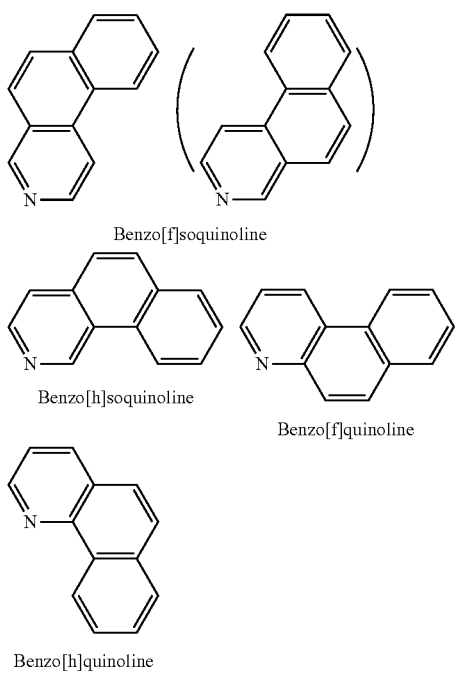

Benzo[f]soquinoline

Benzo[h]soquinoline

Benzo[f]quinoline

Benzo[h]quinoline

The above-mentioned heterocycle is incorporated as a basic skeleton of the bidentate ligand, whereby a light emitting material having high efficiency can be obtained without an emission wavelength being lengthened when a quinoline or an isoquinoline skeleton is used.

As a measure for improving light emitting efficiency of the light emitting material, there are given a measure for suppressing deactivation due to a nonradiative process (hereinafter, referred to as first measure) and a measure for increasing oscillator strength of the material itself (hereinafter, referred to as second measure).

As the first measure, decreasing the number of freely-rotating sites in molecules and the like have been generally known. On the other hand, the second measure largely depends on a structure of the complex or a basic structure of the ligand, whereby it is difficult to control the oscillator strength actively. In particular, increasing the oscillator strength while the emission wavelength is controlled is an important factor in the organic light emitting device, but difficult in practice.

Here, in the organic metal complex of the present invention, a conjugate plane at a pyridine side of the ligand is extended away from the metal atom, and hence a quantum efficiency of the complex itself can be increased.

On the other hand, in the case where electron transition of the exciton which is generated by allowing the light emitting material such as an organic metal complex to excite has a metal to ligand charge transfer (MLCT) property, an electron is transferred from the metal atom side to a bidentate ligand side. When Ir(piq)$_3$ and Compound A1 are taken for example, a conjugate plane that a molecular structure present at a nitrogen-metal coordination side of the bidentate ligand has is extended, and a center of gravity of the conjugate plane is moved to a direction away from the metal atom. From the foregoing, it was found that lengthening a migration length of the electron which transfers from the metal atom to the ligand upon the excitation of the complex was effective for improving the light emitting efficiency. This may be because, owing to the electron transfer from the metal to the ligand and further away therefrom, a dipolar moment of the complex upon the excitation is increased and hence the oscillator strength is improved.

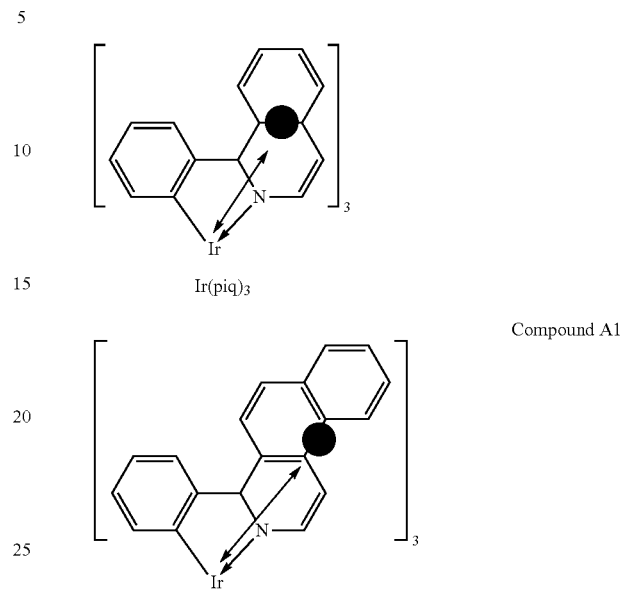

Ir(piq)$_3$

Compound A1

In order to examine the fact, a molecular orbital for a relationship of a distance between the conjugate plane that the metal atom and the ligand in the organic metal complex have and the oscillator strength was calculated. For example, a molecular orbital (nonempirical molecular orbital calculation program: Gaussian, basis function: B3PW91/LANL2DZ) for each organic metal complex represented by one of the following formula was calculated.

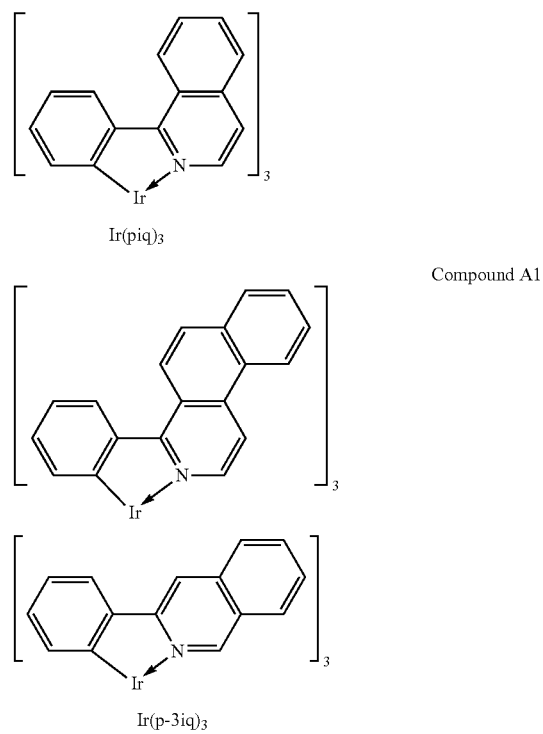

Ir(piq)$_3$

Compound A1

Ir(p-3iq)$_3$

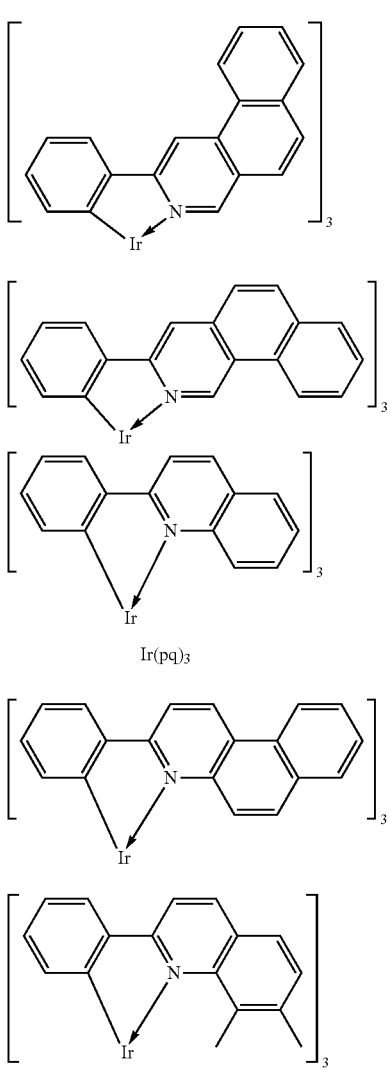

Compound B1

Compound C1

Ir(pq)₃

Compound D1

Compound E1

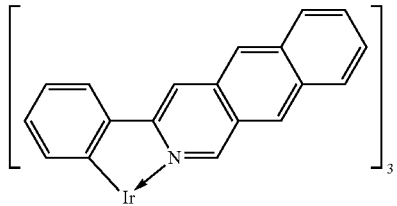

Ir(p-bgiq)₃

As a result, the calculational oscillator strength of Compound A1 was found to be 1.5 times to twice larger than that of Ir(piq)₃. Similarly, it was found that each calculational oscillator strength of Compound B1 and C1 was 1.5 times to twice larger than that of Ir(p-3iq)₃ and each calculational oscillator strength of Compound D1 and E1 was 1.5 times to twice larger than that of Ir(pq)₃. However, those results were the results obtained from calculation, and actual quantum efficiency of the compound may not be reflected to the calculation results. However, the result can be an evidence to support that light emitting characteristics tend to improve due to the structure.

However, when ring structures such as a benzene ring are fused simply, a conjugate length is lengthened for fused components, and therefore, there is the case where the emission wavelength of the compound itself is lengthened. For example, Ir(p-bgiq)₃ represented below lengthen the wavelength by 100 nm or more with respect to Ir(p-3iq)₃ and the emission wavelength of the compound itself becomes 650 nm or more.

Therefore, luminescent color becomes dark red and the emission wavelength is lengthened too much, so the compound is not a suitable light emitting material for an organic EL display.

Then, when the ring structures such as a benzene ring are fused, as shown in the above-mentioned Compounds A1, B1, C1, D1, and E1, heterocyclic skeletons each having a nitrogen atom which forms a coordinate bond with a metal atom are fused in a non-linear form. With the non-linear form, it was found that the oscillator strength could be increased without the emission wavelength being lengthened.

In this point, when the number of the benzene ring present at the nitrogen-metal coordination side of the bidentate ligand is increased, the number of the benzene ring is increased preferably at a position where the benzene ring is not linear with respect to quinoline rings or isoquinoline rings as shown in A1, B1, C1, D1, and E1. Further, for increasing the oscillator strength, the benzene ring is fused to form a ring preferably at as far away as possible from the metal. From the foregoing, the benzene ring is fused to form a ring preferably at f-position or h-position of the quinoline ring or the isoquinoline ring. In particular, each structure of Compounds A1 and B1 can additionally increase the oscillator strength by such points that a center of the conjugate plane at the pyridine side is as far away as possible from the metal atom and a moment of the metal and pyridine and a moment of the metal and the gravity center of conjugate are superposed.

On the other hand, the reason why the wavelength is not lengthened, compared to the case of the quinoline ring or the isoquinoline ring, when a structure at the nitrogen-metal side of the ligand has the structure like Compounds A1, B1, C1, D1, and E1 lies in the above-mentioned fact.

In the organic metal complex of the present invention, an unshared electron pair that the nitrogen atom present in the quinoline skeleton or the isoquinoline skeleton has is used in forming a coordinate bond with the metal atom. Therefore, the nitrogen atom may behave similarly as the carbon atom. In the foregoing, a relationship among three skeletons, i.e., the quinoline skeleton, the isoquinoline skeleton, and the skeleton in which a ring structure is fused to those skeletons, is similar to a relationship among three skeletons, i.e., naphthalene, anthracene, and phenanthrene.

Here, the following description is written in "Handbook of photochemistry" published by Dekker: a triplet excitation energy (T₁) of anthracene in which a benzene ring is fused linearly to naphthalene is 672 nm and the wavelength thereof is indicated to be largely lengthened while T₁ of naphthalene is 469 nm; on the other hand, T₁ of phenanthrene in which a benzene ring is fused non-linearly to naphthalene is 460 nm, and is indicated to be higher than that of naphthalene.

Taking the above-mentioned fact into consideration, emission wavelengths of benzo[f]quinoline, benzo[h]quinoline, benzo[f]isoquinoline, and benzo[h]isoquinoline corresponding to phenanthrene may not be lengthened compared to quinoline and isoquinoline corresponding to naphthalene. Accordingly, a complex containing, as a ligand, benzo[f]quinoline, benzo[h]quinoline, benzo[f]isoquinoline, or benzo[h]isoquinoline is found to have the following characteristics: while a wavelength of the complex is not lengthened with respect to a complex containing a isoquinoline skeleton or a quinoline skeleton, an oscillator strength of the complex itself can be increased and an emission quantum efficiency is improved. Therefore, the complex containing, as a basic skeleton, benzo[f]quinoline, benzo[h]quinoline, benzo[f]isoquinoline, or benzo[h]isoquinoline is excellent as a light emitting material of a phosphorous light emitting material or the like such as an Ir complex.

In addition, Compounds A1, B1, C1, D1, and E1 each have the following properties.

Compound A1 without introducing a substituent can emit a red light, which has a slightly shorter wavelength than that of $Ir(piq)_3$, and the quantum efficiency is also high. Accordingly, when Compound A1 is used as a constituent material of the organic light emitting device, a high-performance device can be provided. In addition, by introducing a substituent, the emission wavelength can be controlled.

Compounds B1 and C1 without introducing a substituent can emit a green light which has a slightly shorter wavelength than that of $Ir(p-3iq)_3$ and the quantum efficiency is high. In addition, by introducing a substituent, the emission wavelength can be controlled.

Compounds D1 and E1 without introducing a substituent can emit an orange light which has a slightly shorter wavelength than that of $Ir(pq)_3$ and the quantum efficiency is high. In addition, by introducing a substituent, the emission wavelength can be controlled.

Thus, a light having a wavelength of green to red, which is important in the organic light emitting device, can be efficiently extracted by selecting a compound appropriately from Compounds A1, B1, C1, D1, and E1.

In addition, it is possible to introduce a substituent into a ligand forming the organic metal complex of the present invention in order to impart steric hindrance to the complex. Thus, a solubility of the ligand upon synthesis of the complex is improved. In addition, from the foregoing, concentration quenching is suppressed, so doping at high concentration is enabled and the light emitting efficiency is expected to be improved when the organic metal complex is used as a constituent material of the device. Here, examples of the substituent for imparting the steric hindrance to the complex include substituents which avoid approaching of luminous ligands to each other, such as a methyl group, a tert-butyl group, and a phenyl group, and substituents which induce repulsion of molecules to each other, such as halogen atoms. By introducing those substituents, even when doping of concentration as high as 5 wt % or more with respect to matrix is occurred, a light can be emitted without reducing a light emitting efficiency.

On the other hand, when the ring structure such as a benzene ring is fused linearly as the above-mentioned $Ir(p-bgiq)_3$, a part which is weak to oxidation and is highly reactive such as 9-position or 10-position in an anthracene skeleton, for example, is generated. Therefore, as $Ir(p-bgiq)_3$, a compound having a skeleton in which ring structures such as a benzene ring are linearly fused may not be preferred as a constituent material for an organic light emitting device.

By the way, in the ligand forming the organic metal complex of the present invention, as a basic skeleton containing a carbon atom which forms a coordinate bond with a metal atom, a benzene ring is mainly exemplified, but a skeleton other than a benzene ring may also be used as long as the skeleton has the structure containing a carbon atom which forms a coordinate bond with a metal atom. By appropriately controlling the basic skeleton containing a carbon atom which forms a coordinate bond with a metal atom, an emission wavelength of the organic metal complex itself can be controlled. Examples of the basic skeleton include a naphthalene ring, a fluorene ring, a carbazole ring, a vinyl skeleton, and a pyridine ring, in addition to the benzene ring.

In addition, the organic metal complex of the present invention may have a molecular structure in which ligands of the same kind are coordinated to the metal atom or may have a molecular structure in which two kinds of ligands having different structures are coordinated from a viewpoint of controlling a molecular weight and a wavelength.

Here, in the case where the complex has the structure in which ligands of the same kind are coordinated to the metal atom, the complex has high symmetric property to the metal atom, and hence has such high heat stability and high electrical stability that the metal complex is not easily decomposed upon deposition. In addition, introduction of a substituent enables lengthening a distance from another light emitting molecules. Therefore, even with doping of as high concentration as 10% or higher to 100%, a light can be emitted while reduction of the light emitting efficiency is suppressed. On the other hand, in the case where the complex has the structure in which two kinds of ligands having different structures are coordinated to the metal atom, the complex has such properties that a deposition temperature can be adjusted by adjustment of the molecular weight and the emission wavelength can be controlled by using an electronic effect of a ligand which does not emit a light. In addition, the number of ligands relating to light emitting can be reduced from 3 ligands to 2 ligands or 1 ligand. Therefore, a concentration quenching can be expected to be suppressed and even with doping of as high concentration as 10% or higher to 100%, a light can be emitted while reduction of the light emitting efficiency is suppressed.

In addition, the organic metal complex of the present invention has steric constitutional isomers, i.e., a fac body and a mer body. The organic metal complex of the present invention may have one of the structures but preferably the fac body which may generally have high quantum efficiency. However, in the case where the complex has the structure in which two kinds of ligands having different structures are coordinated to the metal atom, even the mer body such as $Ir(ppy)_2acac$ may have high quantum efficiency. Therefore, the fac body may not be necessarily preferred. In addition, when the complex is synthesized, it is difficult to synthesize one of constitutional isomers alternatively and a mixture of both isomers may be used from the aspect of cost.

Specific examples of the organic metal complex of the present invention are described below. However, the present invention is not limited thereto.

A1 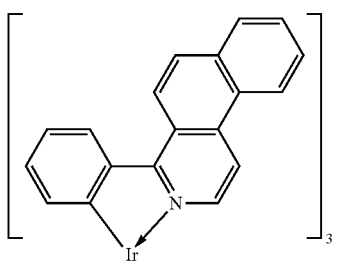
A2 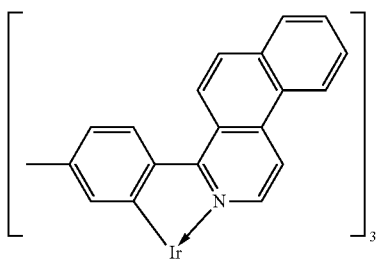
A3 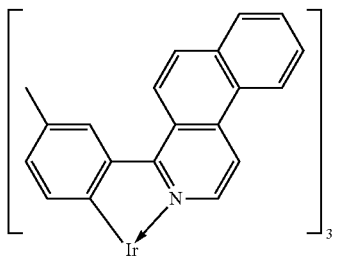
A4 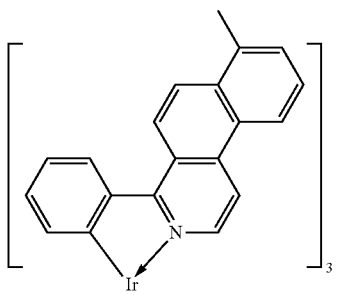
A5 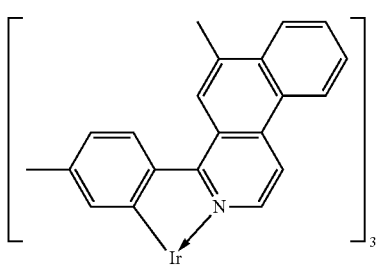
A6 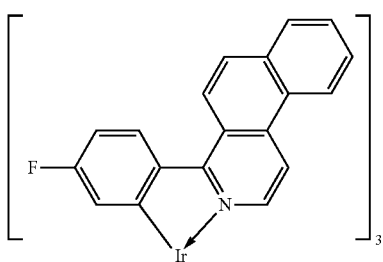
-continued
A7 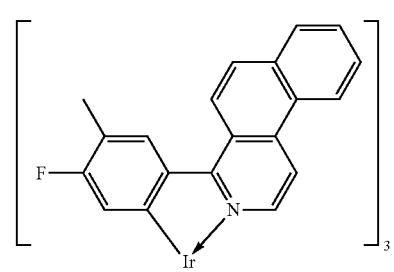
A8 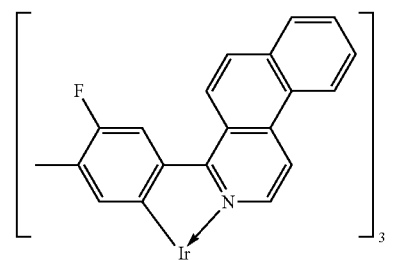
A9 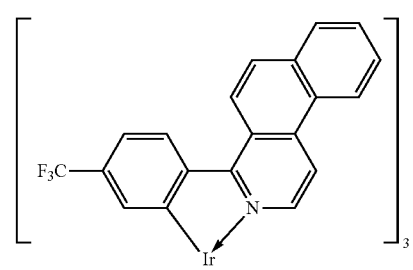
A10 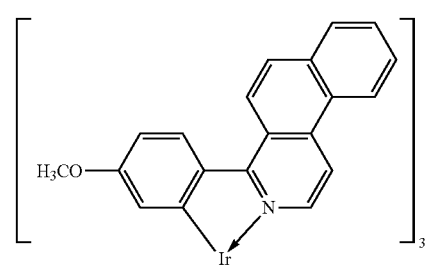
A11 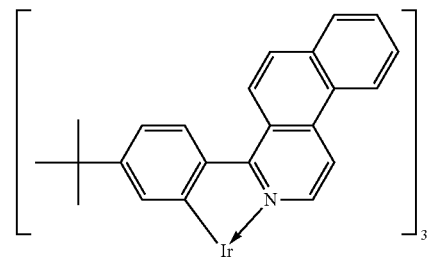
A12 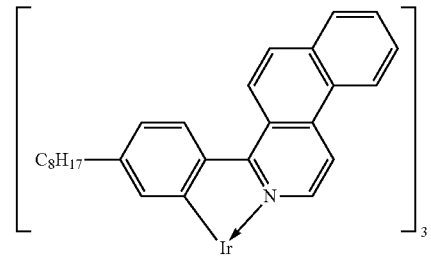

-continued
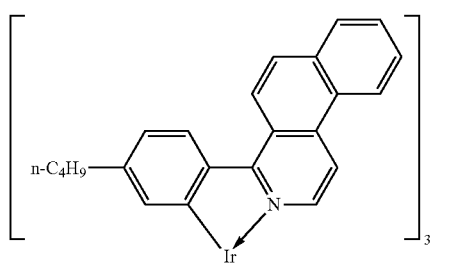
A13
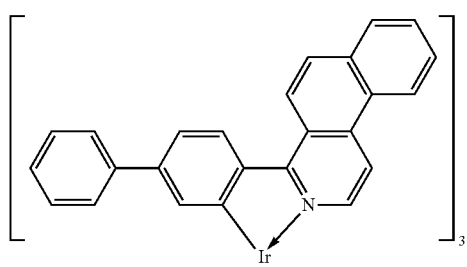
A14
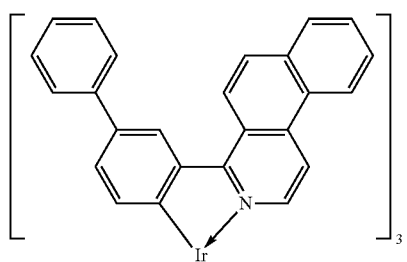
A15
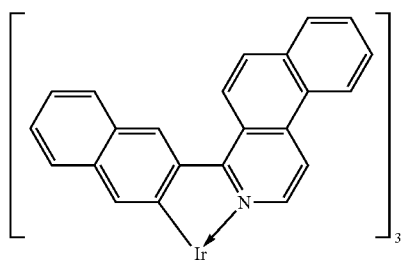
A16
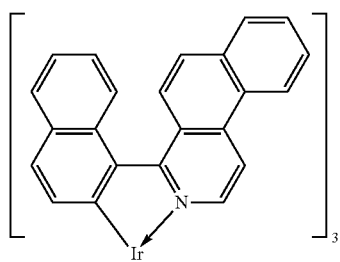
A17
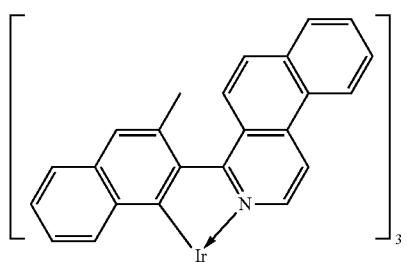
A18
-continued
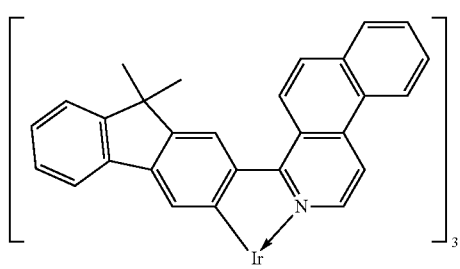
A19
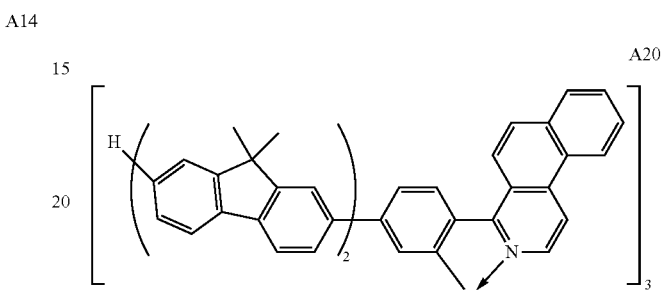
A20
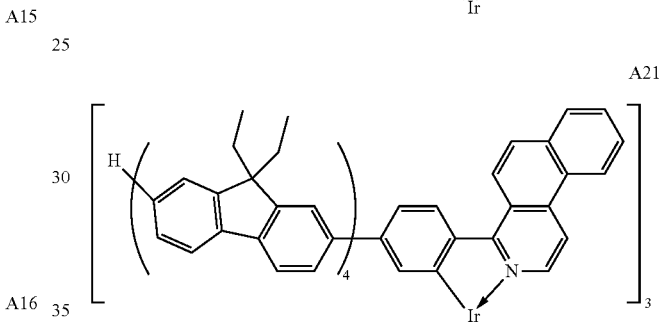
A21
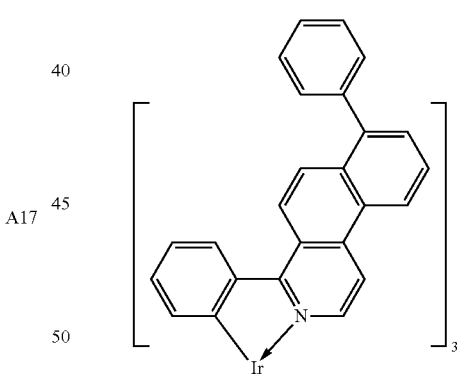
A22
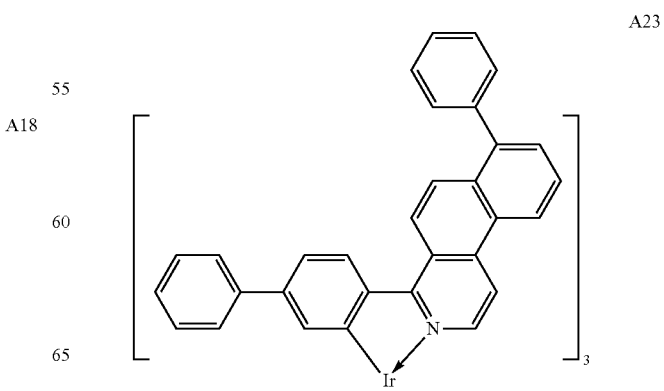
A23

-continued
A24
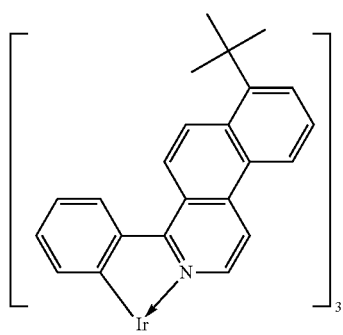
A25
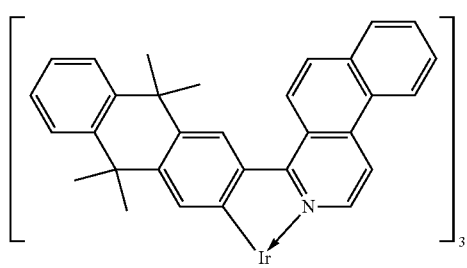
A26
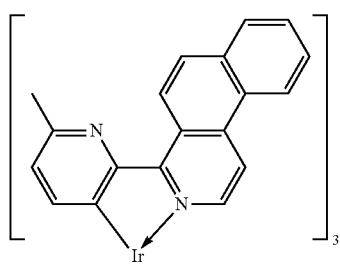
A27
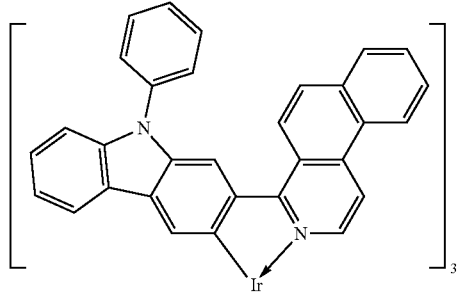
A28
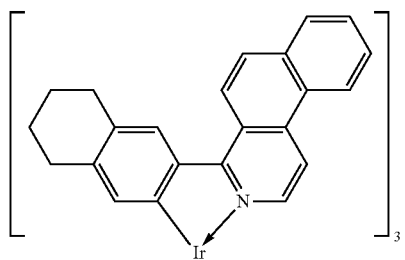
-continued
A30
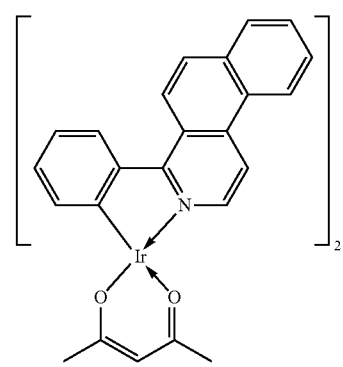
A31
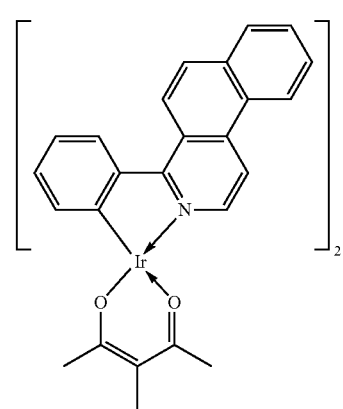
A32
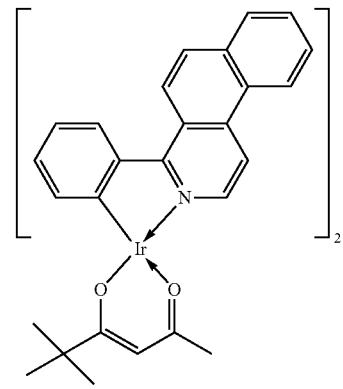
A33
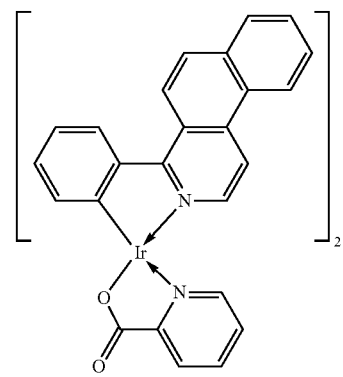

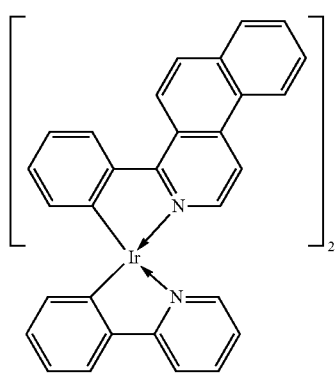
A34
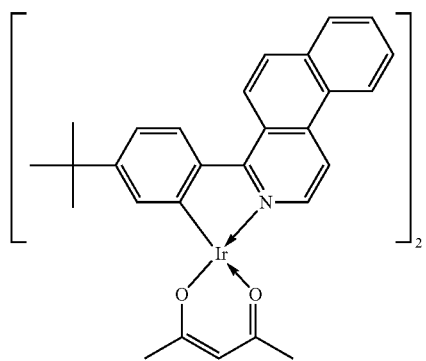
A35
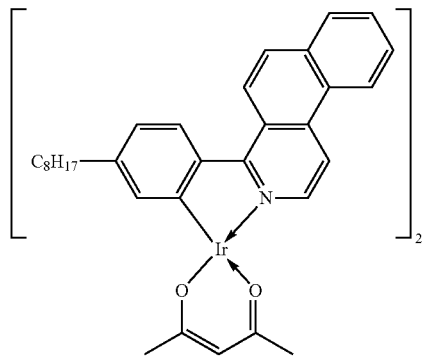
A36
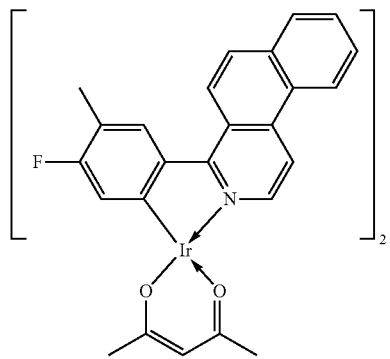
A37
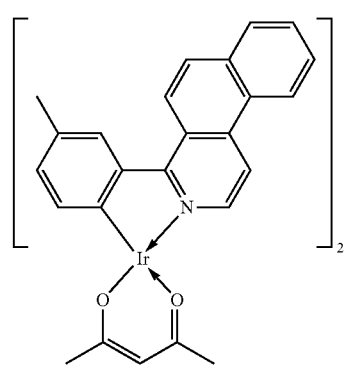
A38
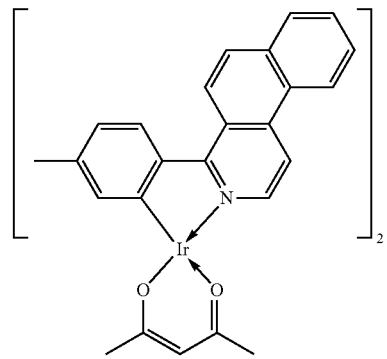
A39
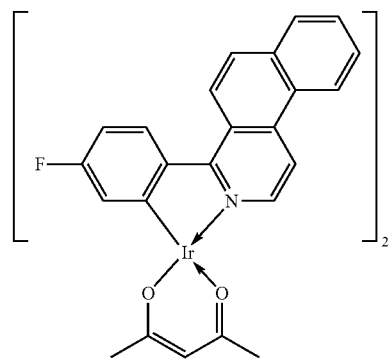
A40
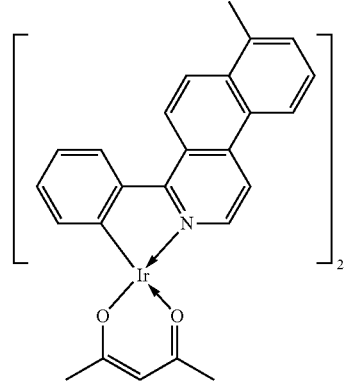
A41

A42
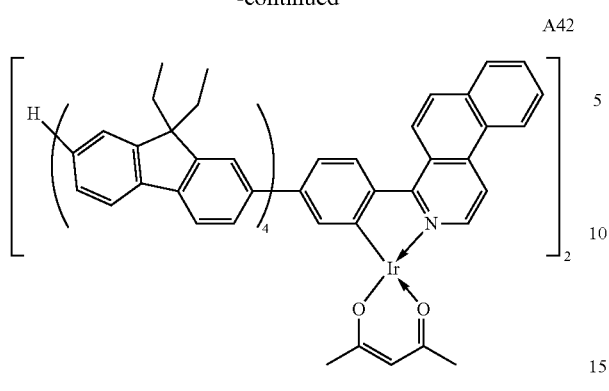
A46
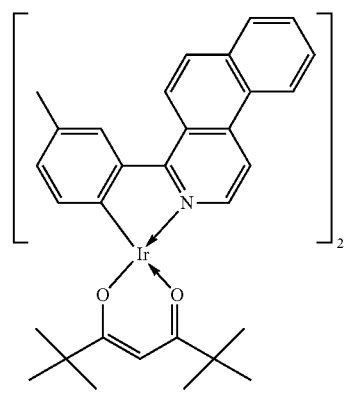
A43
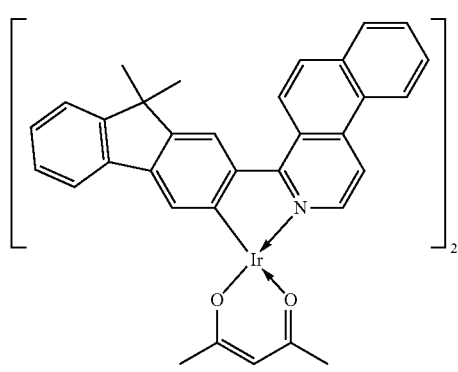
A47
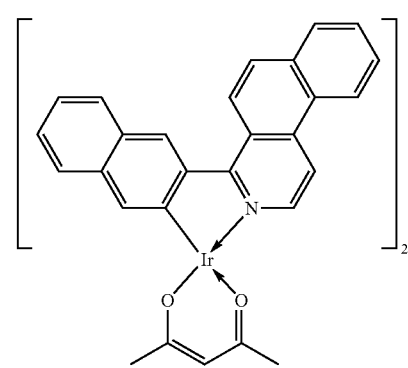
A44
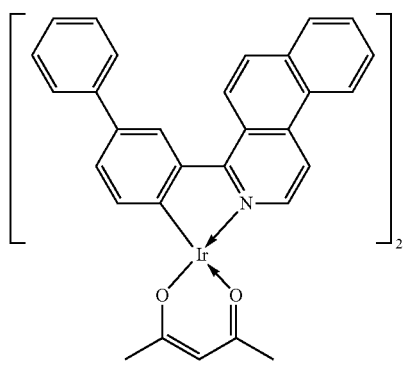
A48
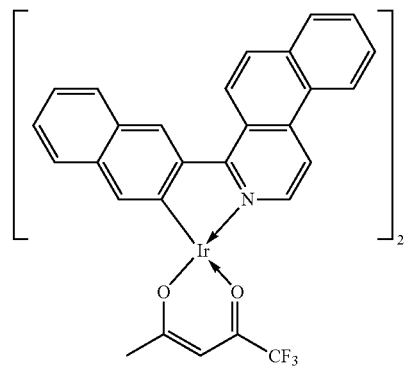
A45
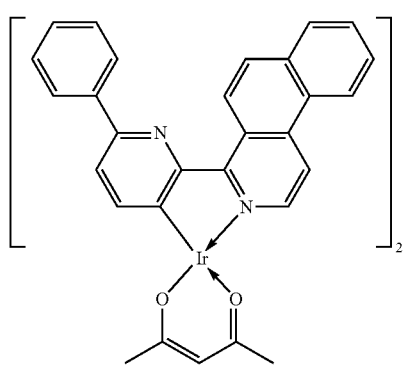
A49

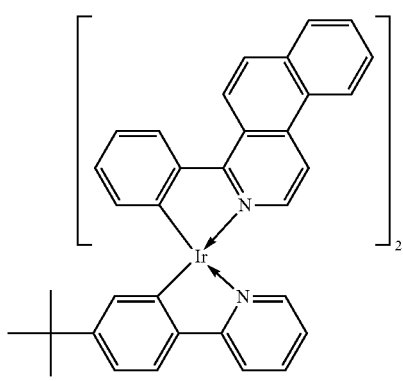
A50
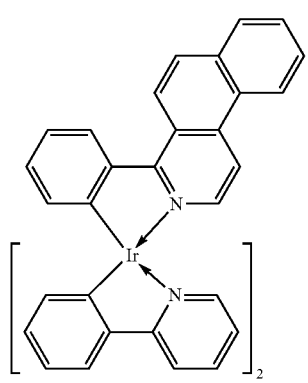
A51
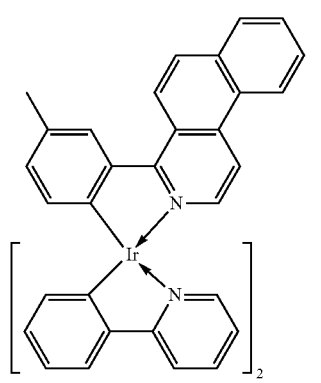
A52
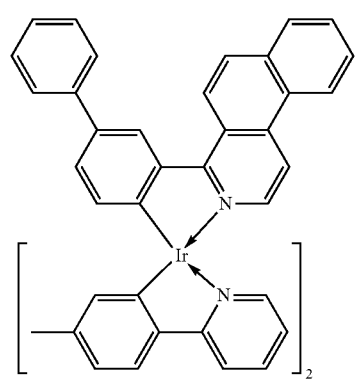
A53
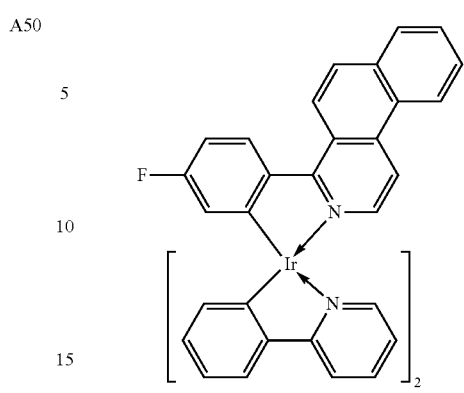
A54
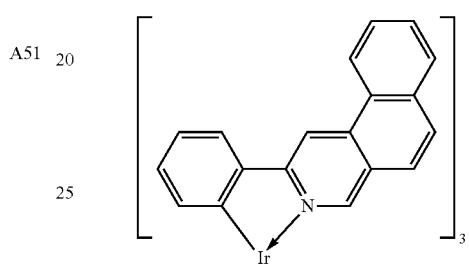
B1
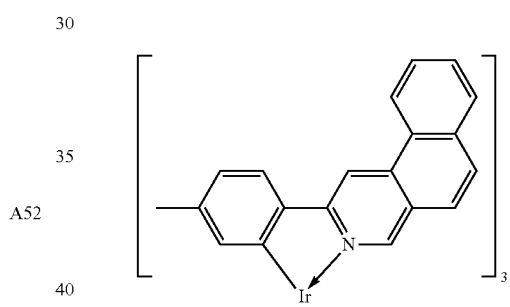
B2
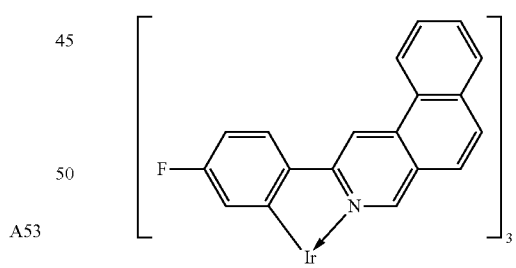
B3
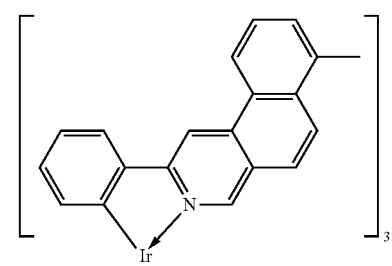
B4

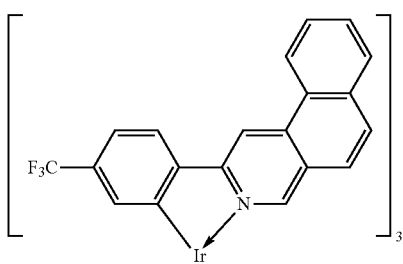
B5
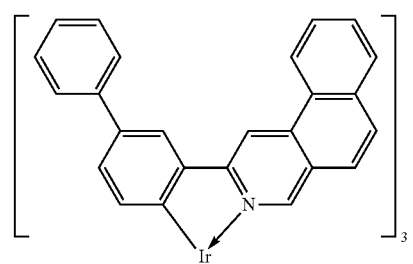
B11
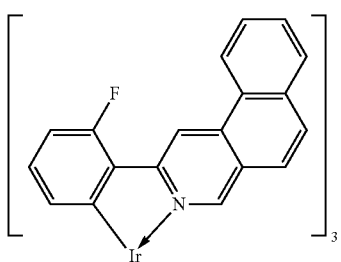
B6
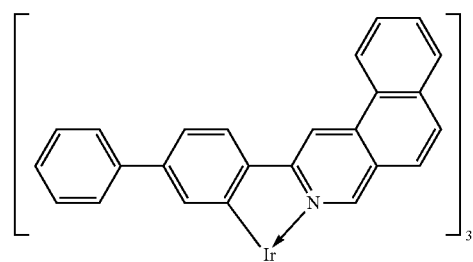
B12
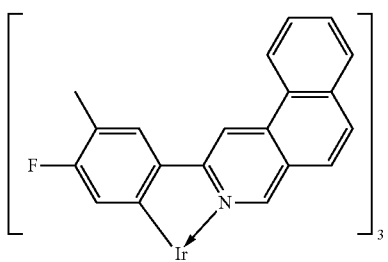
B7
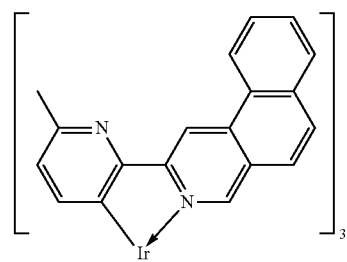
B13
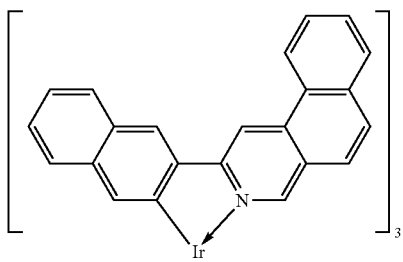
B8
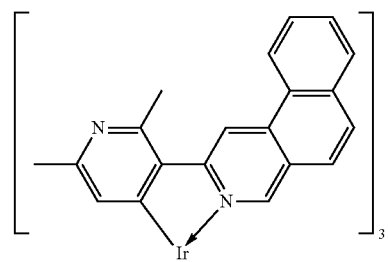
B14
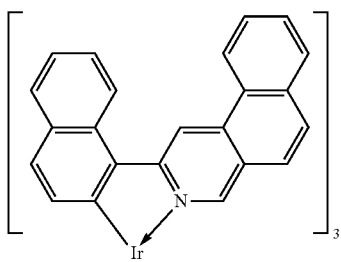
B9
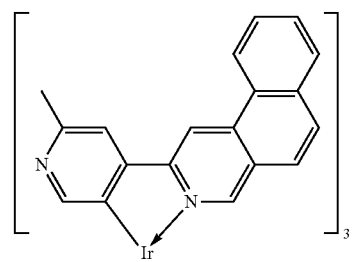
B15
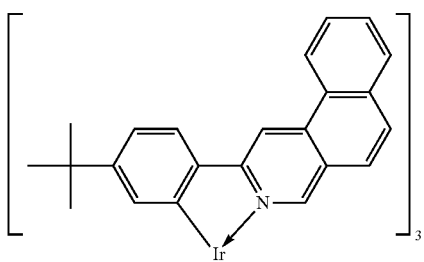
B10
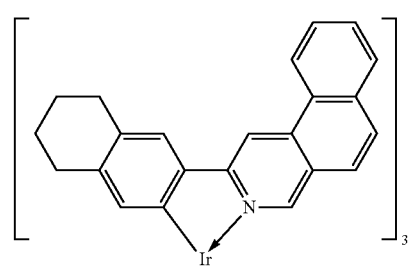
B16

B17
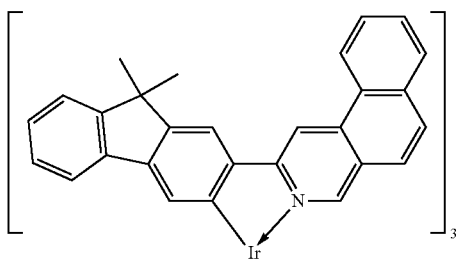
B22
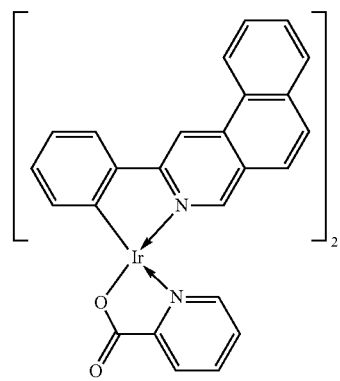
B18
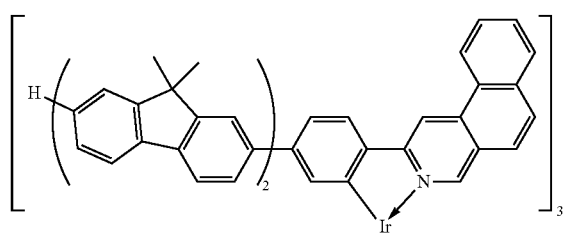
B19
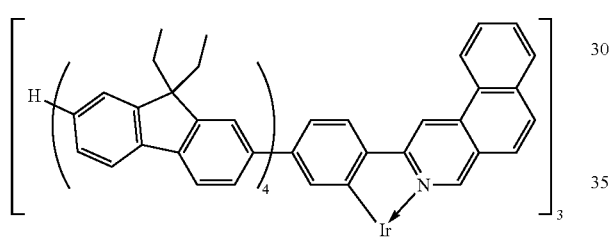
B23
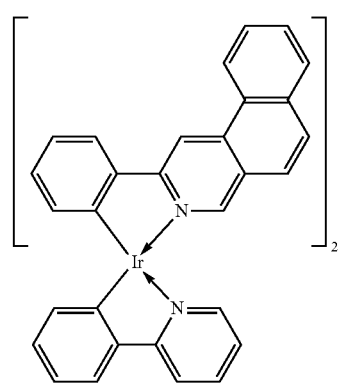
B20
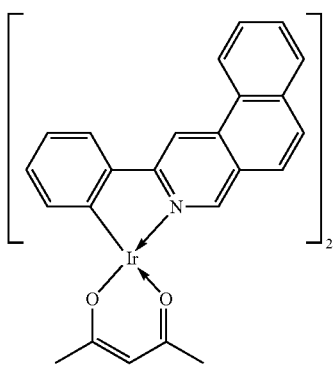
B24
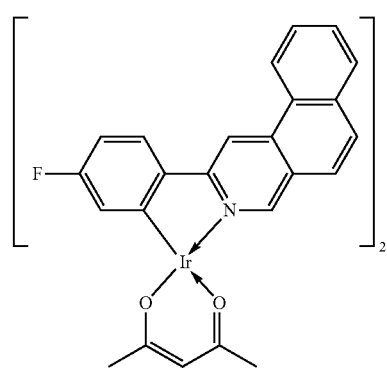
B21
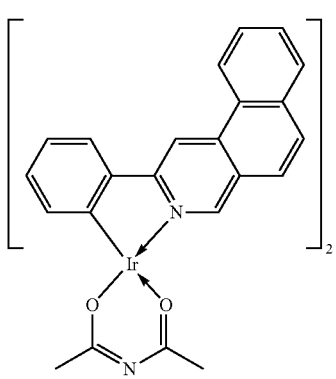
B25
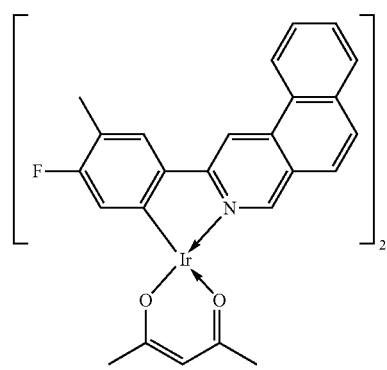

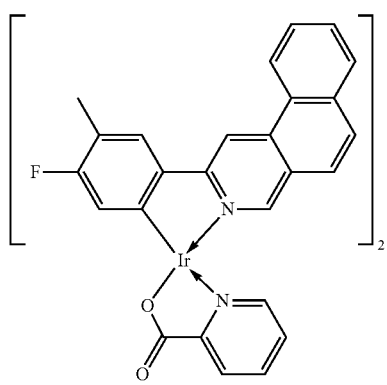
B26
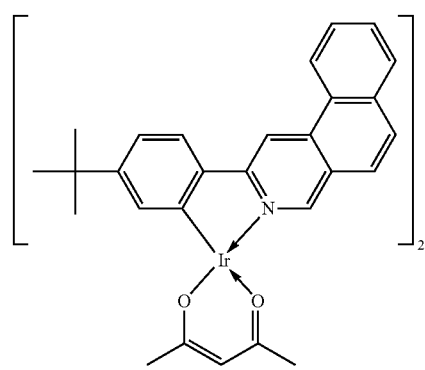
B30
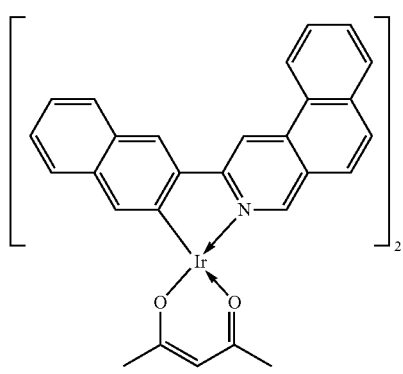
B27
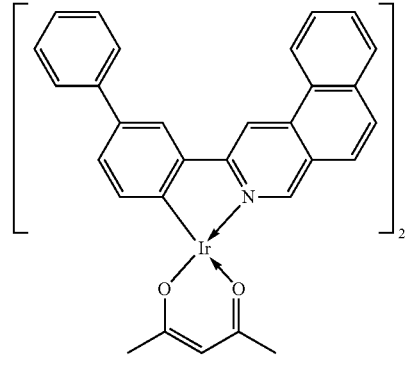
B31
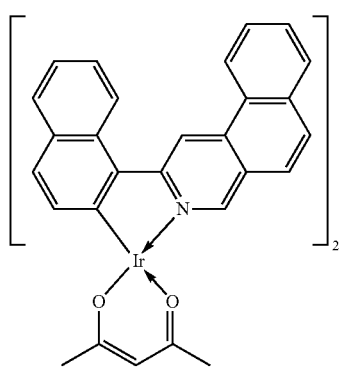
B28
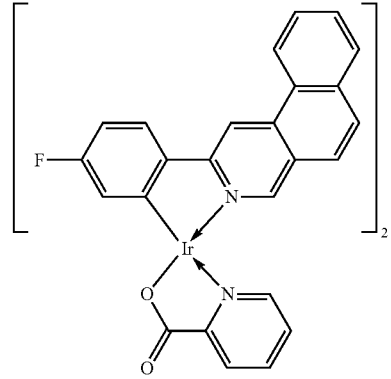
B32
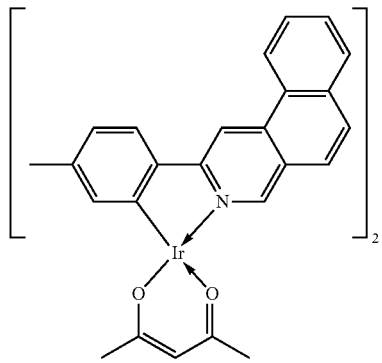
B29
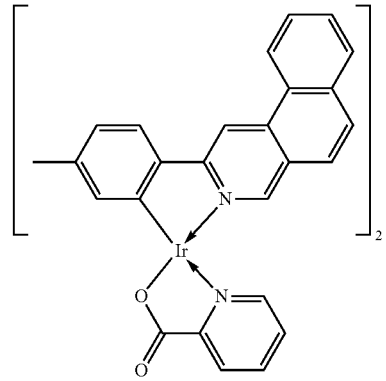
B33

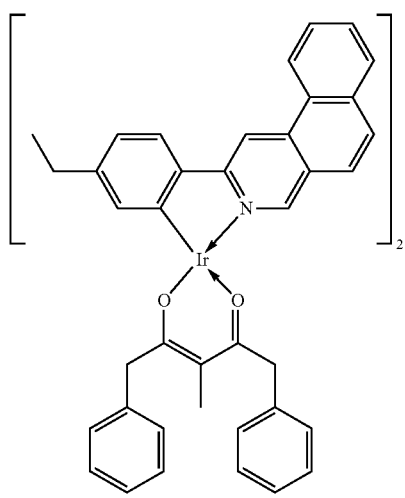
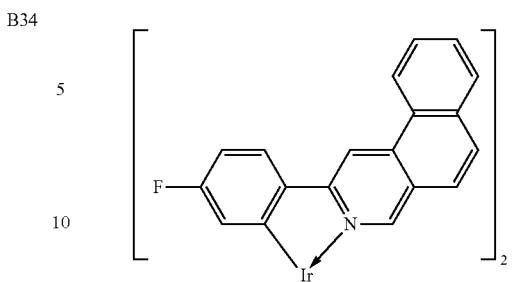

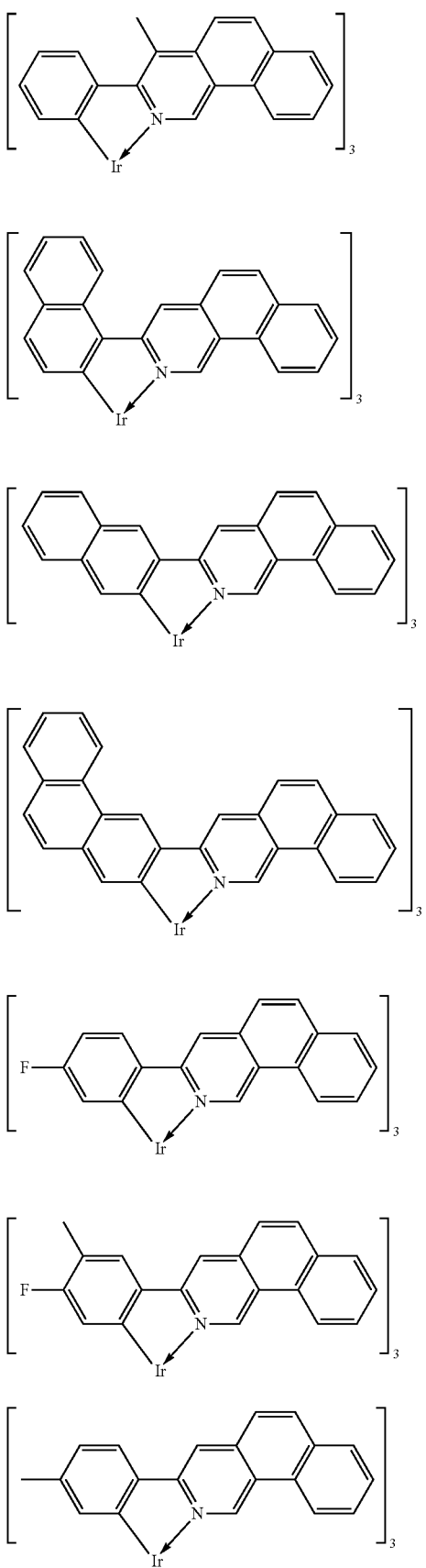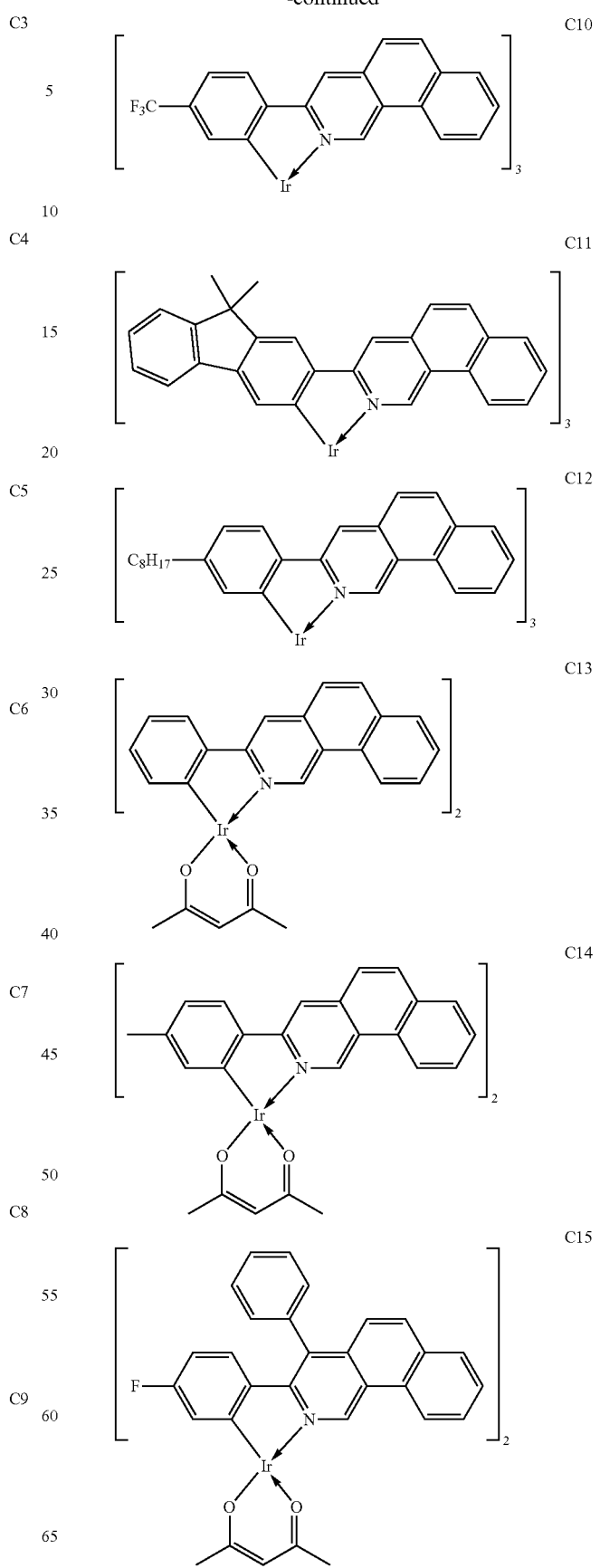

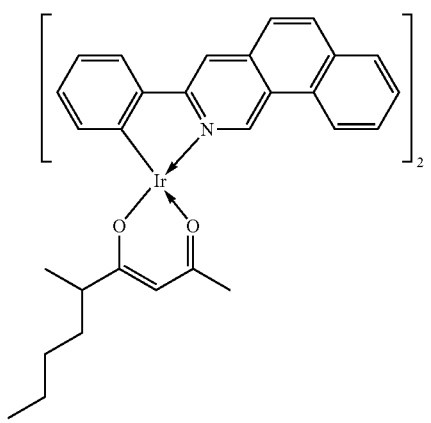
C16
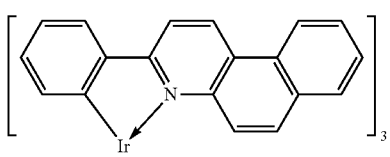
D1
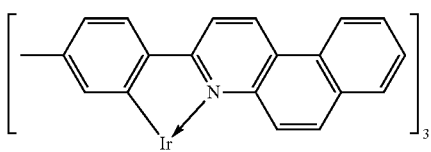
D2
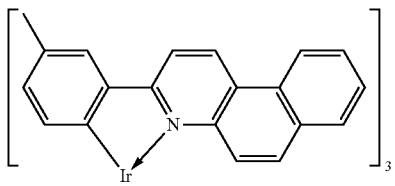
D3
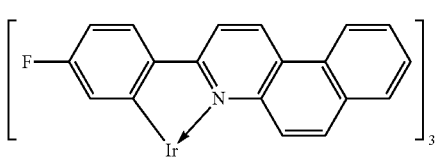
D4
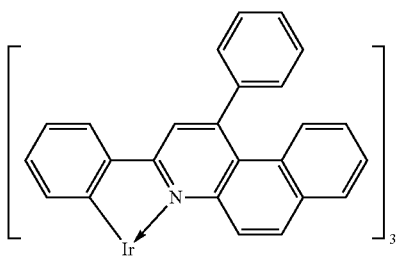
D5
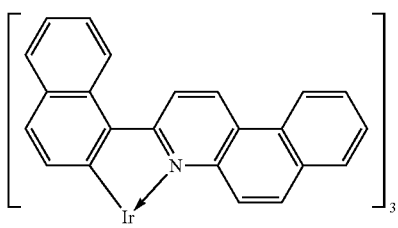
D6
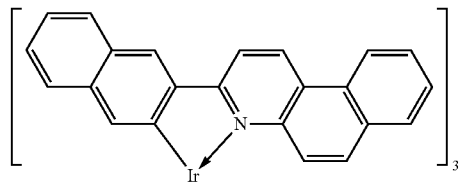
D7
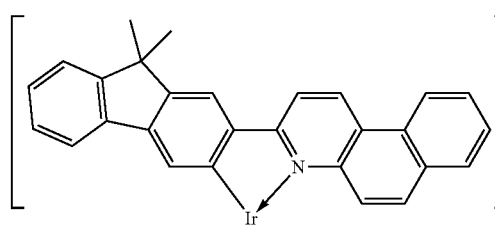
D8
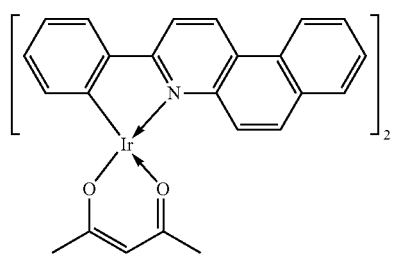
D9
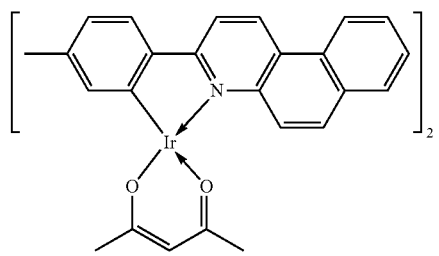
D10
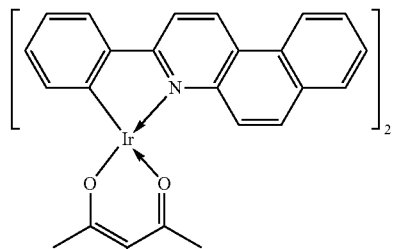
D11
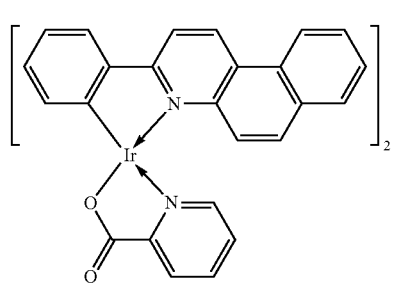
D12

-continued
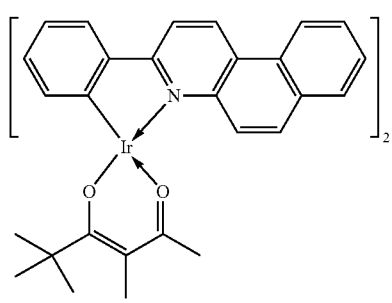 D13
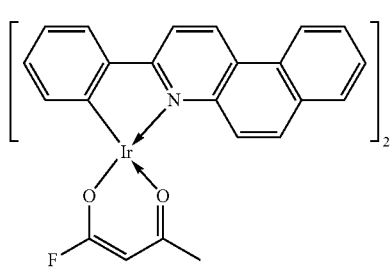 D14
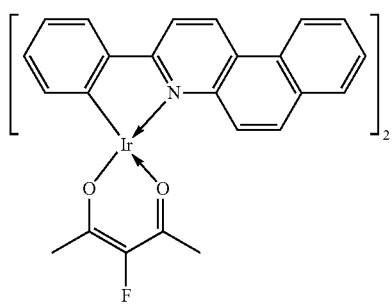 D15
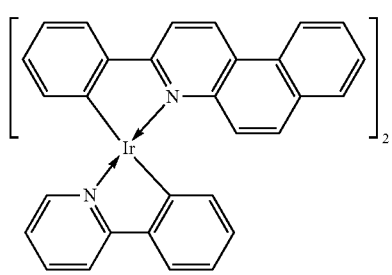 D16
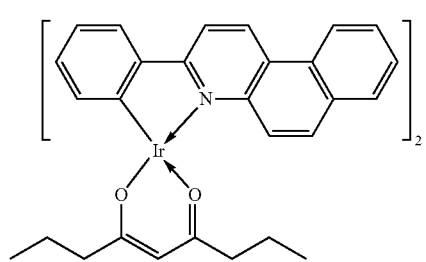 D17
-continued
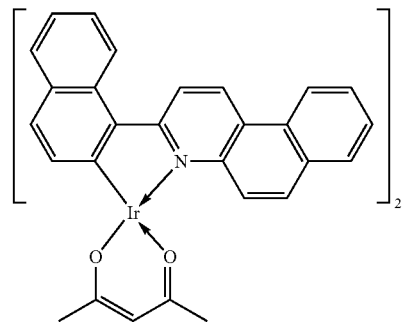 D18
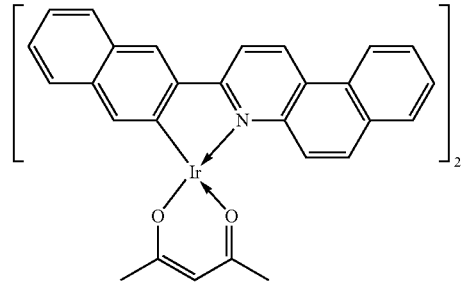 D19
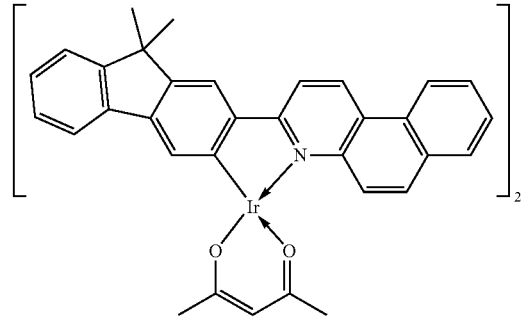 D20
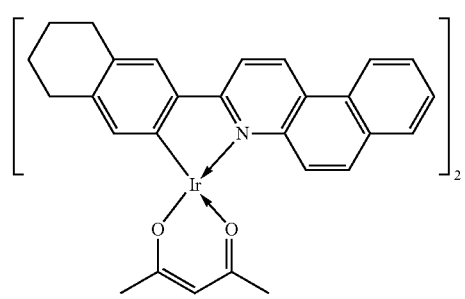 D21
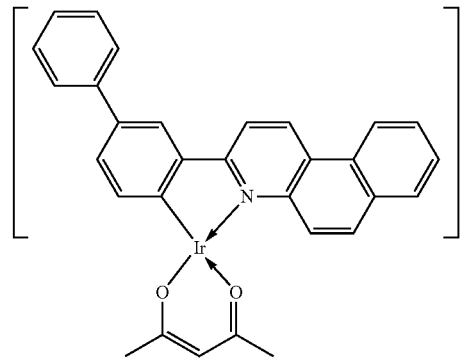 D22

-continued
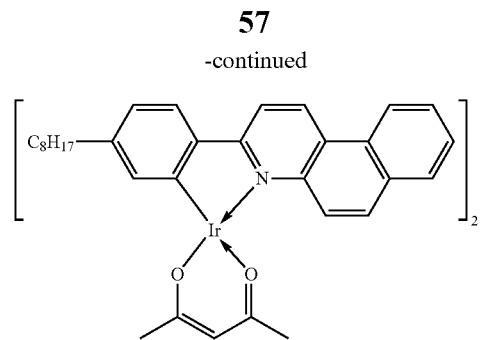
D23
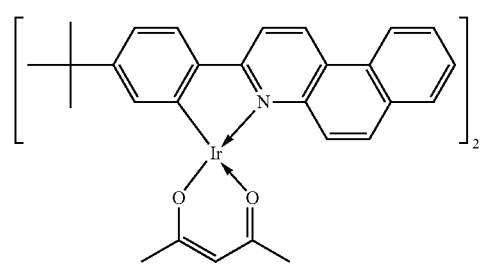
D24
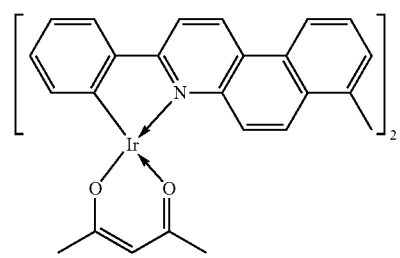
D25
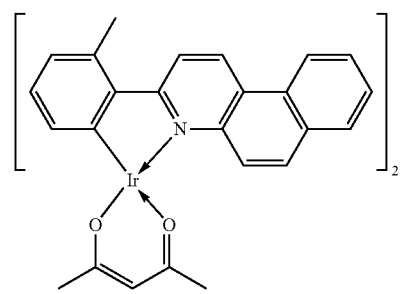
D26
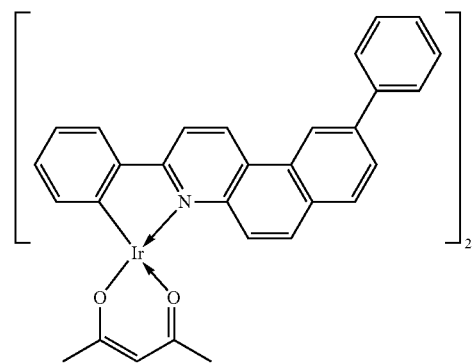
D27
-continued
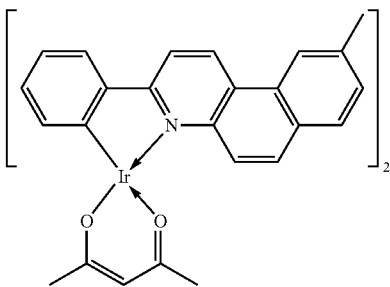
D28
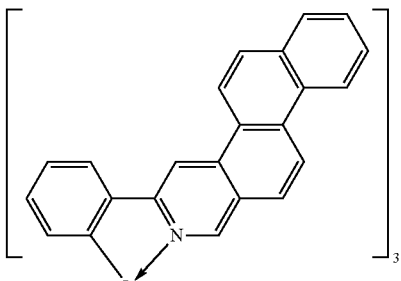
E1
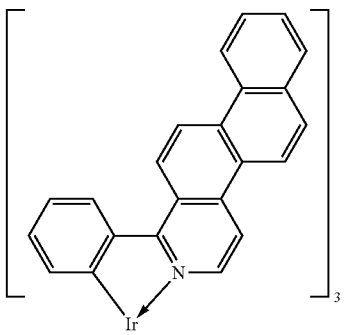
E2
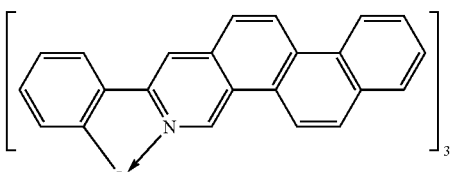
E3
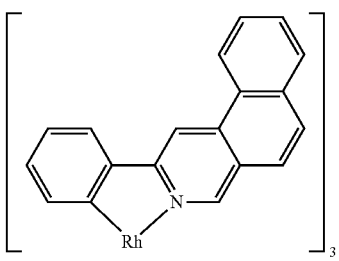
E4
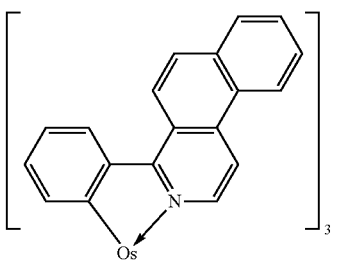
E5

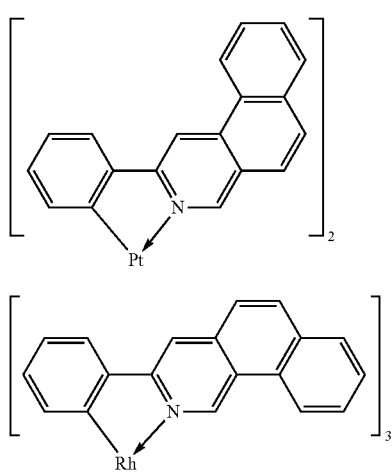

Next, the organic light emitting device of the present invention is described in detail.

The organic light emitting device of the present invention includes an anode, a cathode, and a layer formed of an organic compound, which is sandwiched between the anode and the cathode.

Hereinafter, embodiments of the organic light emitting device of the present invention are described.

A first embodiment of an organic light emitting device according to the present invention includes the anode, the organic emission layer, and the cathode, which are sequentially formed on a substrate. The first embodiment is useful in a case where the emission layer is formed of an organic compound which has all the properties including a hole transporting ability, an electron transporting ability, and light emitting property. Further, in a case where the emission layer is formed of a mixture of compounds each having one of the hole transporting ability, the electron transporting ability, and the light emitting property.

A second embodiment of the organic light emitting device according to the present invention includes the anode, a hole transport layer, an electron transport layer, and the cathode, which are sequentially formed on the substrate. The second embodiment is useful in a case where an organic compound which is a light emitting substance having one of hole transporting property and electron transporting property and an organic compound having electron transporting property alone or hole transporting property alone are used in combination. In addition, in this second embodiment, the hole transport layer or the electron transport layer serves as the emission layer.

A third embodiment of the organic light emitting device according to the present invention includes the anode, the hole transport layer, the emission layer, the electron transport layer, and the cathode, which are sequentially formed on the substrate. The third embodiment provides the light emitting device, in which a carrier transporting function and a light emitting function are separated from each other. Thus, the device can be used appropriately in combination with organic compounds each having one of the hole transporting property, electron transporting property, and light emitting property. Therefore, in the third embodiment, the degree of freedom in selection of a material extremely increases as well as various compounds different from each other in emission wavelength can be used. As a result, the range of luminescent colors can be widened. Further, a light emitting efficiency of the organic light emitting device can be improved by effectively trapping each carrier or exciton in the central emission layer.

A fourth embodiment of the organic light emitting device according to the present invention includes the anode, a hole injection layer, the hole transport layer, the emission layer, and the cathode, which are sequentially formed on the substrate. In the fourth embodiment, the provision of the hole injection layer in between the anode and the hole transport layer imparts an improving effect on adhesiveness and the hole injection property, and is effective for a reduction in voltage at which the device is driven.

A fifth embodiment of the organic light emitting device according to the present invention includes the anode, the hole transport layer, the emission layer, a hole/exciton blocking layer, the electron transport layer, and the cathode, which are sequentially formed on substrate. In the fifth embodiment, a layer for inhibiting the escape of a hole or exciton toward the side of the cathode, which is the hole/exciton blocking layer, is provided between the emission layer and the electron transport layer. The use of a composition material having an extremely high ionization potential as a constituent material of the hole/exciton blocking layer is effective for improving the light emitting efficiency.

It should be noted that the device structures as described in the first to fifth embodiments are each merely very basic device structure, and the structure of the organic light emitting device of the present invention is not limited thereto. A variety of a layer structure may be provided. For example: an insulating layer, an adhesive layer, or an interference layer may be provided onto an interface between an electrode and an organic compound, and a hole transport layer may be formed of two layers having different ionization potentials.

In the organic light emitting device of the present invention, the organic metal complex of the present invention can be used in any one of the first to fifth embodiments. Here, the organic light emitting device of the present invention includes the organic metal complex of the present invention in a layer formed of an organic compound (organic compound layer). Here, the term "organic compound layer" refers to, for example, any one of the hole injection layer, the hole transport layer, the emission layer, the hole/exciton blocking layer, and the electron transport layer indicated in the first to fifth embodiments. Preferred is the emission layer.

In the organic light emitting device of the present invention, the emission layer may be formed only of the organic metal complex of the present invention, but preferably formed of a host and a guest. Here, the term "guest" refers to a compound having mainly a function of light emission. On the other hand, the term "host" refers to a compound present as a matrix around the guest in the emission layer and mainly having a function of transporting a carrier and a function of providing an exciton energy to the guest.

Here, in the case where the emission layer of the organic light emitting device is formed of a host having a carrier transporting property and a guest, a main process to the light emission includes the following several processes. Energy transfer and light emission in respective processes are caused by competition with various deactivation processes.

(1) Transport of an electron and a hole inside the emission layer (2) Exciton generation of the host, Exciton generation of the guest 1

(3) Exciton energy transmittance among host molecules (4) Exciton energy transfer from the host to the guest, exciton generation of the guest 2
(5) light emission from guest molecules In general, in order to increase the light emitting efficiency of the organic light emitting device, an emission central material itself is desired to have large light emitting quantum efficiency.

Here, the organic metal complex of the present invention has high quantum efficiency of light emission in a dilute solution, whereby high light emitting efficiency can be expected in the case of using the organic metal complex of the present invention as a constituent material for the organic light emitting device.

In the organic light emitting device according to the present invention, in the case of using the organic metal complex of the present invention as a guest (dopant), examples of the corresponding host include iridium compounds, compounds shown in Table 1, and derivatives thereof.

TABLE 4

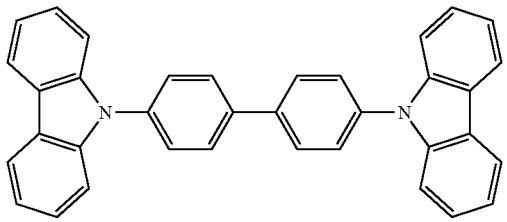 [SMILES: c1ccc2c(c1)c1ccccc1n2-c1ccc(-c2ccc(-n3c4ccccc4c4ccccc43)cc2)cc1]

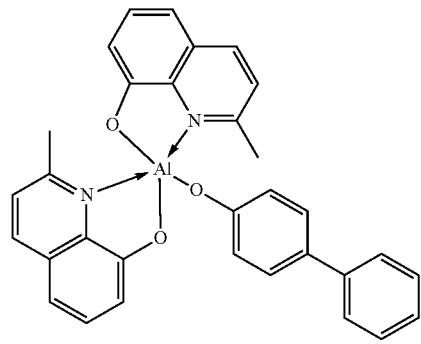

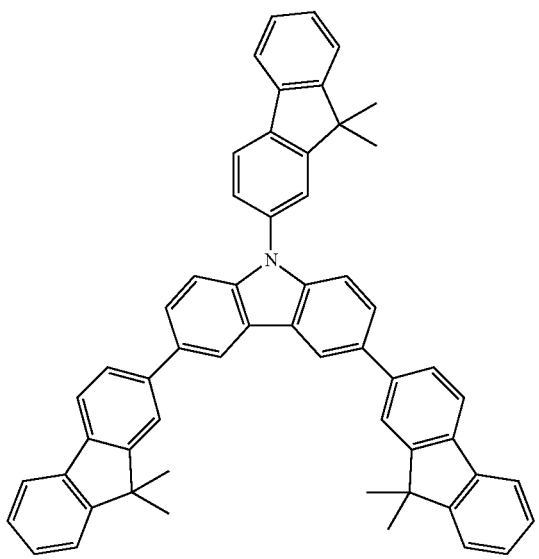 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]

TABLE 4-continued
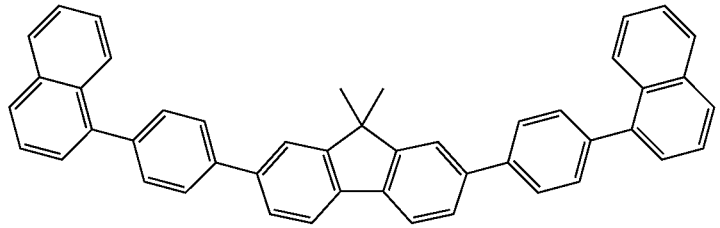 [SMILES: CC1(C)c2cc(-c3ccc(-c4cccc5ccccc45)cc3)ccc2-c2ccc(-c3ccc(-c4cccc5ccccc45)cc3)cc21]
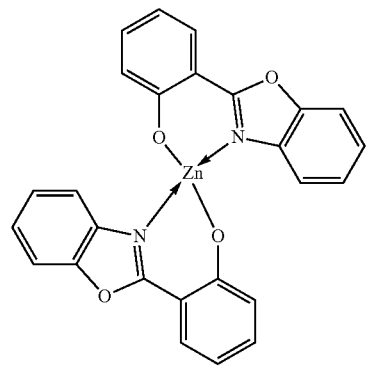
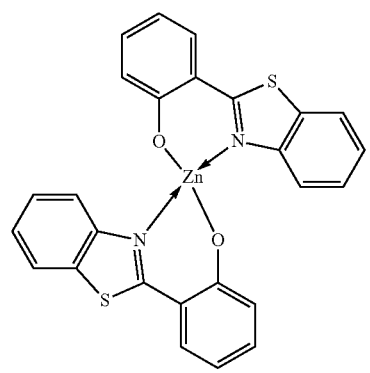
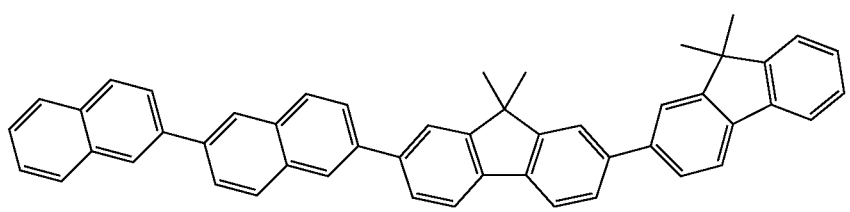 [SMILES: CC1(C)c2ccccc2-c2ccc(-c3ccc4c(c3)C(C)(C)c3cc(-c5ccc6cc(-c7ccc8ccccc8c7)ccc6c5)ccc3-4)cc21]
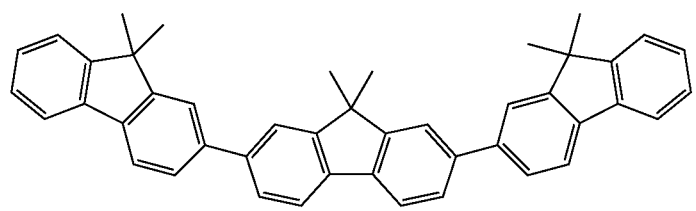 [SMILES: CC1(C)c2ccccc2-c2ccc(-c3ccc4c(c3)C(C)(C)c3cc(-c5ccc6c(c5)C(C)(C)c5ccccc5-6)ccc3-4)cc21]

TABLE 4-continued
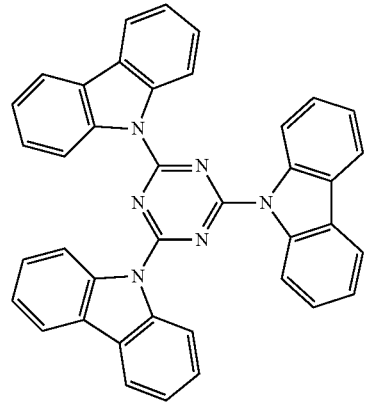 [SMILES: c1ccc2c(c1)c1ccccc1n2-c1nc(-n2c3ccccc3c3ccccc32)nc(-n2c3ccccc3c3ccccc32)n1]
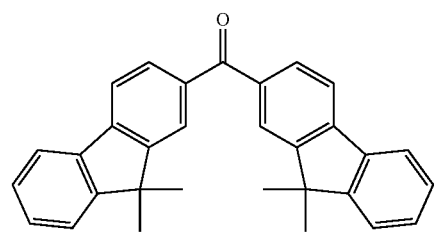 [SMILES: CC1(C)c2ccccc2-c2ccc(C(=O)c3ccc4c(c3)C(C)(C)c3ccccc3-4)cc21]
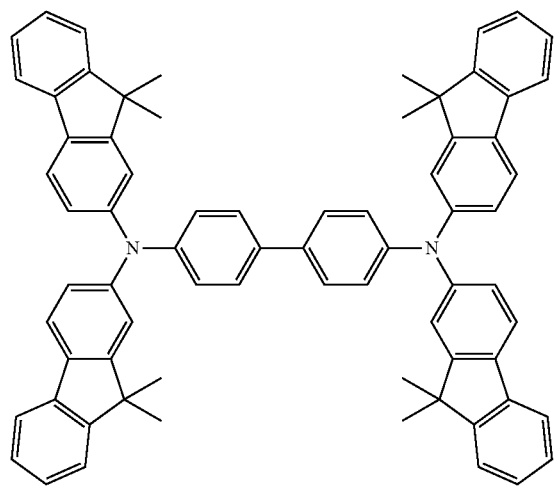 [SMILES: CC1(C)c2ccccc2-c2ccc(N(c3ccc(-c4ccc(N(c5ccc6c(c5)C(C)(C)c5ccccc5-6)c5ccc6c(c5)C(C)(C)c5ccccc5-6)cc4)cc3)c3ccc4c(c3)C(C)(C)c3ccccc3-4)cc21]
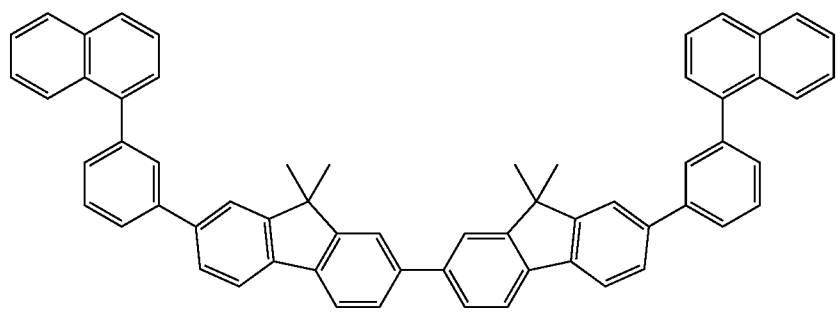 [SMILES: CC1(C)c2cc(-c3cccc(-c4cccc5ccccc45)c3)ccc2-c2ccc(-c3ccc4c(c3)C(C)(C)c3cc(-c5cccc(-c6cccc7ccccc67)c5)ccc3-4)cc21]

TABLE 4-continued
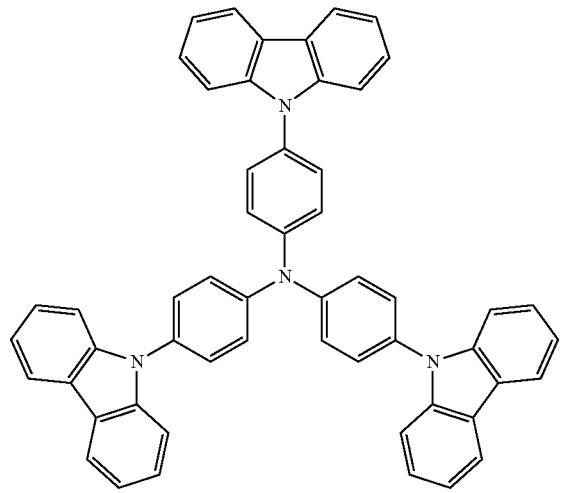 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]
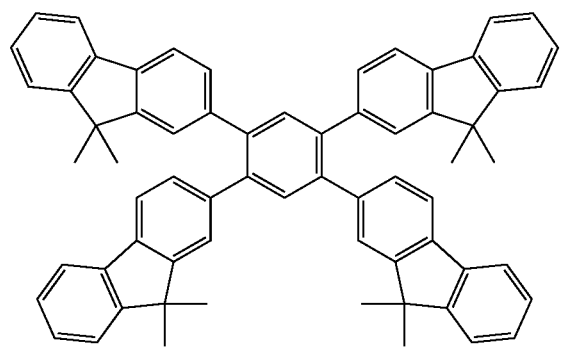 [SMILES: CC1(C)c2ccccc2-c2ccc(-c3cc(-c4ccc5c(c4)C(C)(C)c4ccccc4-5)c(-c4ccc5c(c4)C(C)(C)c4ccccc4-5)cc3-c3ccc4c(c3)C(C)(C)c3ccccc3-4)cc21]
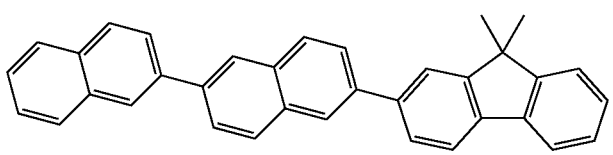 [SMILES: CC1(C)c2ccccc2-c2ccc(-c3ccc4cc(-c5ccc6ccccc6c5)ccc4c3)cc21]
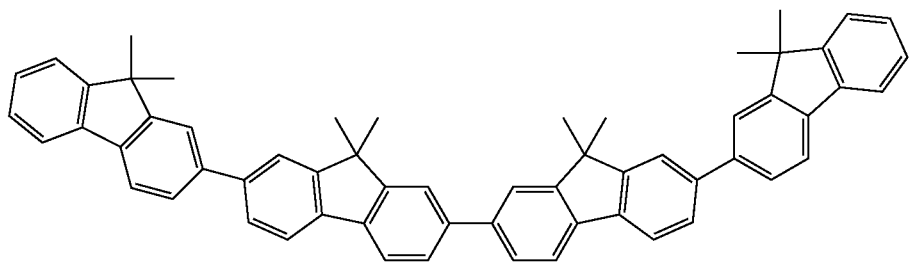 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

TABLE 4-continued

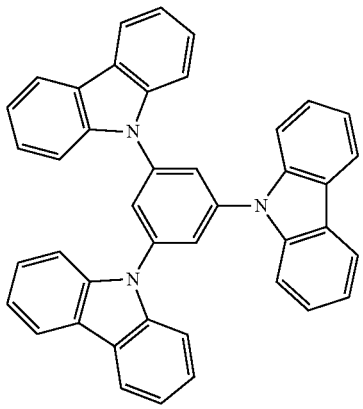 [SMILES: c1ccc2c(c1)c1ccccc1n2-c1cc(-n2c3ccccc3c3ccccc32)cc(-n2c3ccccc3c3ccccc32)c1]

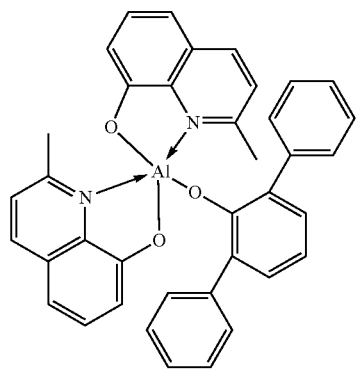

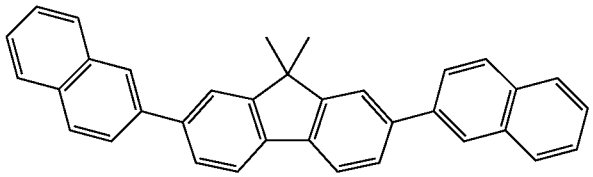 [SMILES: CC1(C)c2cc(-c3ccc4ccccc4c3)ccc2-c2ccc(-c3ccc4ccccc4c3)cc21]

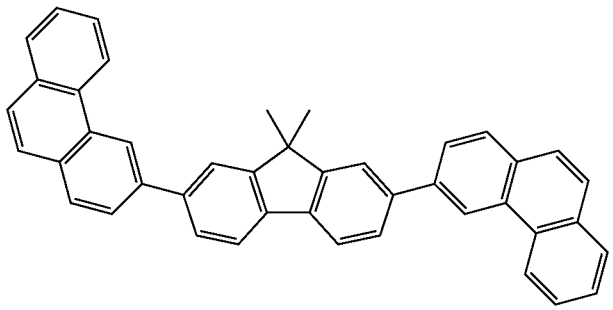 [SMILES: CC1(C)c2cc(-c3ccc4ccc5ccccc5c4c3)ccc2-c2ccc(-c3ccc4ccc5ccccc5c4c3)cc21]

In addition to the above compounds, there are given, but of course the host is not limited to, a fused-ring compounds (such as fluorene derivatives, naphthalene derivatives, carbazole derivatives, quinoxaline derivatives, and quinoline derivatives), organic aluminum complexes such as tris(8-quinolilato)aluminum, organic zinc complexes, triphenyl amine derivatives, polymer derivatives such as poly(fluorene) derivatives, and poly(phenylene) derivatives.

In addition, in the case of the organic metal complex of the present invention as a guest (dopant), a concentration of the guest is preferably 0.01 wt % to 20 wt %, and more preferably 0.5 wt % to 10 wt % with respect to the host. In addition, by controlling the concentration of the guest, the emission wavelength of the device can be lengthened by about 5 nm to 20 nm.

Here, a compound having a hole transporting property, and a compound having a light emitting property, or a compound having an electron transporting property, each of which is a conventionally-known low-molecular-weightbased or polymer compound-based, can be used, as required, together with the organic metal complex of the present invention.

Hereinafter, examples of those compounds are given.

As the material having a hole injecting property, a material having a high hole transfer degree is preferred to facilitate the injection of a hole from an anode and to transport the injected hole to the emission layer. Examples of the low-molecular-weight-based or polymer-based material each having a hole injecting property include, but are not limited to, triarylamine derivatives, phenylenediamine derivatives, stilbene derivatives, phthalocyanine derivatives, porphyrin derivatives, poly(vinylcarbazole), poly(thiophene), and other conductive polymers.

As the material having a light emitting property, $Ir(ppy)_3$, $Pt(OEP)$, $Ir(piq)_3$, $Alq_3$, rubrene, coumarine, and the like are exemplified in addition to the organic metal complex of the present invention.

The electron injection transporting material may be arbitrarily selected from compounds each of which facilitates the injection of an electron from a cathode and has a function of transporting the injected electron to the emission layer. In addition, the material is selected in consideration of, for example, a balance with the hole mobility of the hole transporting material. The materials having electron injection transporting abilities include, but are of course not limited to, an oxadiazole derivative, an oxazole derivative, a pyrazine derivative, a triazole derivative, a triazine derivative, a quinoline derivative, a quinoxaline derivative, a phenanthroline derivative, and an organoaluminum complex.

As a material for constituting an anode, a material having as large a work function as possible is preferred. Examples of available materials include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, and polythiophene may also be used. Each of those electrode substances may be used singly. Alternatively, two or more of them may also be used in combination. Further, the anode may adopt any one of a single layer construction and a multilayer construction.

On the other hand, as a material constituting a cathode, a material having as small a work function as possible is preferred. Examples of available materials include: alkali metals such as lithium, alkali earth metals such as calcium, and metal elements such as aluminum, titanium, manganese, silver, lead, and chromium. Alternatively, alloys in combination of those metal elements may also be used. For example, magnesium-silver, aluminum-lithium, and aluminum-magnesium can be used. Further, metal oxides such as indium tin oxide (ITO) may also be used. Each of those electrode substances may be used singly or in combination of two or more. Further, the cathode may adopt any one of a single layer construction and a multilayer construction.

Substrates which may be used in the organic light emitting device of the present invention include: opaque substrates such as metallic substrates and ceramics substrates; and transparent substrates such as glass, quartz, and plastic sheet substrates, but are not particularly limited to these materials. In addition, a color filter film, a fluorescent color converting film, a dielectric reflection film, or the like may be used in the substrate to control emitted light.

It should be noted that, a protective layer or a sealing layer may be formed on the prepared device to prevent the device from contacting with oxygen, moisture, or the like. The protective layer may include a diamond thin film, a film made of an inorganic material such as metal oxide or metal nitride, a polymer film made of a fluorine resin, polyethylene, a silicone resin, a polystyrene resin, or the like, or may include a photo-curing resin or the like. Further, the device itself can be covered with glass, a gas-impermeable film, a metal, or the like and packaged with an appropriate sealing resin.

Moreover, with respect to a direction of extracting light of the device, both a bottom emission structure (structure in which light is extracted from the substrate side) and a top emission structure (structure in which light is extracted from a side opposite to the substrate) can be acceptable.

In the organic light emitting device of the present invention, a layer containing the organic metal complex of the present invention and a layer containing another organic compound are formed by a method described below. In general, such layers are produced using a vacuum deposition method, ionization-assisted deposition method, a sputtering method, or a plasma method, or a thin film may be formed by dissolving the compound in a suitable solvent and subjecting the resultant to a known coating method (e.g., a spin coating method, a dipping method, a casting method, an LB method, an ink jet method, etc.). Here, a layer formed by the vacuum deposition method, a solution coating method, or the like is preferred because crystallization is less likely to occur and has excellent stability with time. In film formation by the coating method, a film may be formed by using a compound in combination with an appropriate binder resin.

When the coating method is used, an oligomer or a polymer material may be used as a host. In this time, the oligomer or the polymer material can be mixed with the organic metal complex of the present invention and then coated, whereby a thin film having a good film-forming property can be obtained.

The organic light emitting device is produced specifically in the following processes.

(a) An ITO is patterned on a glass substrate to form an anode.
(b) PEDOT (for organic EL) manufactured by Bayer AG is dropped on the anode and spin-coated, followed by drying to form a hole transport layer.
(c) A coating solution prepared from H-4 shown below, A21 (a weight mixing ratio: H-4/A21=10/1), and a solvent is dropped and spin-coated, followed by drying to form an emission layer.

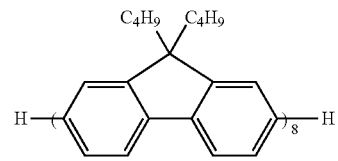

H-4

(d) An electron transport layer such as Bphen is deposited under vacuum.
(e) KF is deposited under vacuum, whereby a first metal electrode is formed.
(f) Al is deposited under vacuum, whereby a second metal electrode is formed.

Examples of the binder resin include, but of course are not limited to, a polyvinylcarbazole resin, a polycarbonate resin, a polyester resin, an ABS resin, an acrylic resin, a polyimide resin, a phenol resin, an epoxy resin, a silicone resin, and a urea resin. In addition, these binder resins each may be formed of a homopolymer or a copolymer. In addition, one kind of the binder resin may be used alone or a mixture of two or more kinds may be used. Further, a known additive such as plasticizer, an antioxidant, or a UV absorber, as required, may be used in combination.

By various known ideas, the organic light emitting device of the present invention can be improved in light-extraction efficiency, color purity, and the like. For example, by processing a shape of a substrate surface (for example, forming a fine concavo-convex pattern), controlling refractive indices of the substrate, the ITO layer, or the organic layer, controlling film thickness of the substrate, the ITO layer, or the organic layer, and the like, the light-extraction efficiency and the external quantum efficiency can be improved. In addition, by methods involving reducing extra wavelength component as a result of using a microcavity structure (fine resonator structure) or obtaining a desired color as a result of providing a color filter, the color purity can be improved.

The organic light emitting device of the present invention may be a so-called top emission system in which a light emission is extracted from an anode side for the purpose of improving an aperture ratio or may be a cavity structure in which the color purity is adjusted by a light interference.

The organic light emitting device of the present invention can be applied to products which requires energy conservation and high luminance. The device may be applied to image display apparatuses, a light source of printers, lighting equipment, backlight of liquid crystal displays, and the like.

As the image display apparatuses, an energy-conservation flat panel display having high visibility and light-weight are exemplified.

In addition, as the light source of a printer, a laser light source part of a laser beam, which is widely used at present, can be substituted by the organic light emitting device of the present invention. As the method of substituting, a method involving arranging, on an array, an organic light emitting device which can address independently is exemplified. Even if the laser light source part is substituted by the organic light emitting device of the present invention, an image is formed by exposing to a photosensitive drum desirably as is conventionally done. Here, according to use of the organic light emitting device of the present invention, a volume of the printer can be largely reduced.

An energy conservation effect can be expected in the lighting equipment and the backlight by using the organic light emitting device of the present invention.

Next, the display apparatus using the organic light emitting device of the present invention is described. The display apparatus is provided with the organic light emitting device of the present invention and a unit for supplying an electrical signal to the organic light emitting device of the present invention. Hereinafter, with reference to the figures and taking an active matrix system as an example, the display apparatus of the present invention is described in detail.

First, reference numerals in the figures are described. A display apparatus 1 includes a pixel circuit 14, a scanning signal driver 11, an information signal driver 12, and a current supplying source 13. A pixel circuit 2 includes a first thin film transistor (TFT) 21, a condenser 22 ($C_{add}$), and a second thin film transistor (TFT) 23. A display apparatus 3 includes a substrate 31, a moistureproof layer 32, a gate electrode 33, a gate insulating layer 34, a semiconductor layer 35, a drain electrode 36, a source electrode 37, a TFT device 38, an insulating layer 39, a contact hole 310 (through hole), an anode 311, an organic layer 312, a cathode 313, a first protective layer 314, and a second protective layer 315.

FIG. 1 illustrates an embodiment of a display apparatus. In addition, FIG. 1 illustrates schematically a structural example of the display apparatus including the organic light emitting device of the present invention and a driving unit. In the display apparatus of FIG. 1, the scanning signal driver 11, the information signal driver 12, the current supplying source 13 are provided and the drivers and source are connected to a gate selection line G, an information signal line I, and a current supplying line C, respectively. The pixel circuit 14 is provided on an intersection point of the gate selection line G and the information signal line I. The scanning signal driver 11 selects gate selection lines from G1 to Gn subsequently, and then an image signal is applied to the pixel circuit 14 through any one of information signal lines I1 to In from the synchronized information signal driver 12.

Figure 2:
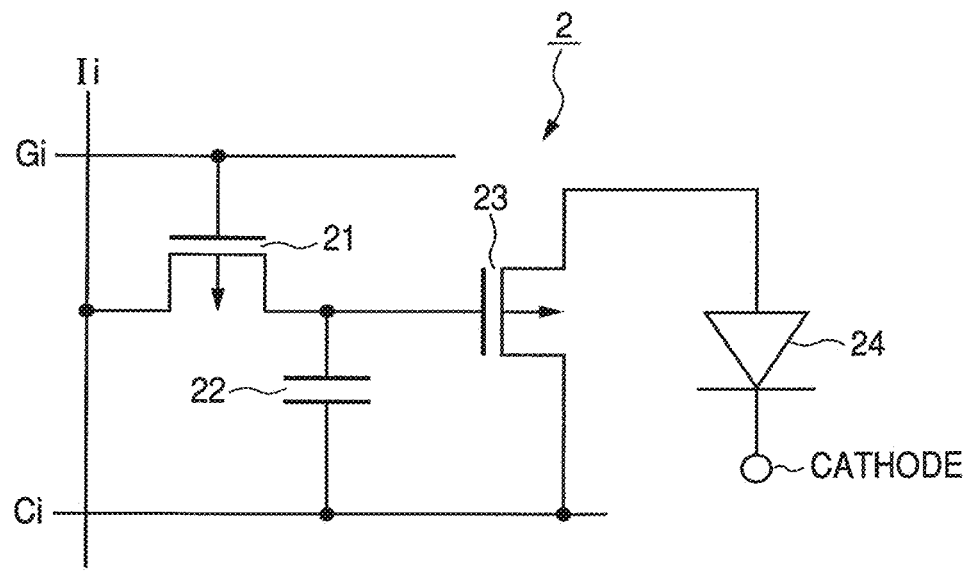
FIG. 2 is a circuit diagram illustrating a circuit which constitutes one of the pixels arranged on the display apparatus shown in FIG. 1.

Next, operation of the pixels is described. FIG. 2 is a circuit diagram illustrating a circuit which forms one pixel provided in the display apparatus of FIG. 1. In the pixel circuit 2 of FIG. 2, when a selection signal is applied to a gate selection line Gi, the first thin film transistor (TFT1) 21 is switched to ON, and then an image signal Ii is supplied to the condenser ($C_{add}$) 22, whereby a gate voltage of the second thin film transistor (TFT2) 23 is determined. To the organic light emitting device 24, a current is supplied from the current supplying line Ci according to the gate voltage of the second thin film transistor (TFT2) 23. Here, the gate voltage of the second thin film transistor (TFT2) 23 is retained by the condenser ($C_{add}$) 22 until the first thin film transistor (TFT1) 21 is next selected for scanning. Therefore, the current continues to be applied to the organic light emitting device 24 until the next scanning is conducted. From the foregoing, the organic light emitting device 24 can emit light consistently during one frame.

Figure 3:
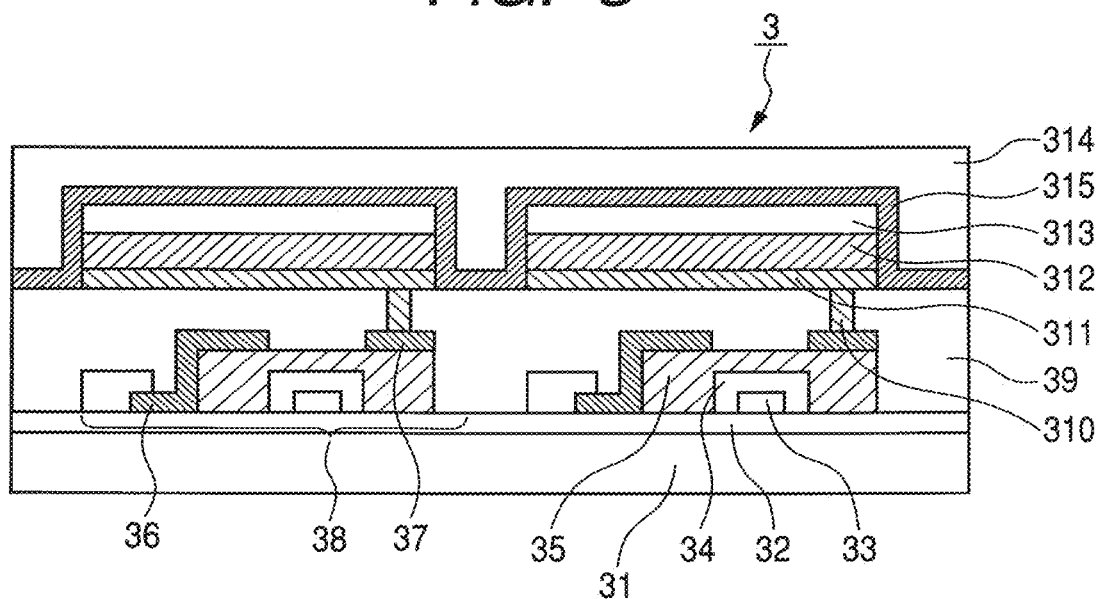
FIG. 3 is a schematic diagram illustrating an example of a cross-sectional structure of a TFT substrate which is used in the display apparatus shown in FIG. 1.

FIG. 3 is a schematic drawing illustrating an example of a cross sectional structure of a TFT substrate used in the display apparatus of FIG. 1. The structure is described in detail below by illustrating one example of a production process of the TFT substrate. When the display apparatus 3 of FIG. 3 is produced, the moistureproof layer 32 is coated on the substrate 31 such as a glass to protect a member (a TFT or an organic layer) provided above the substrate. As a material forming the moistureproof layer 32, silicon oxide, a complex of silicon oxide and silicon nitride, or the like is used. Next, a metal such as Cr is formed into a film by sputtering, whereby the metal is patterned into a predetermined circuit shape to form the gate electrode 33. Subsequently, silicon oxide or the like is formed into a film by a plasma CVD method, a catalytic chemical vapor deposition method (cat-CVD method), or the like, and the film is then patterned to form the gate insulating layer 34. Next, by the plasma CVD method (in some cases, annealed at a temperature of 290° C. or higher), a silicon film is formed and pattered according to the circuit shape, whereby the semiconductor layer 35 is formed.

Further, the drain electrode 36 and the source electrode 37 are provided on the semiconductor layer 35, whereby the TFT device 38 is produced to form the circuit as shown in FIG. 2. Next, the insulating layer 39 is formed above the TFT device 38. Then, the contact hole (through hole) 310 is formed so that the anode 311 for the organic light emitting device formed of a metal and the source electrode 37 are connected.

On the anode 311, the organic layer 312 formed of a single layer or a multilayer, and the cathode 313 are laminated subsequently, whereby the display apparatus 3 can be obtained. At this time, in order to prevent degradation of the organic light emitting device, the first protective layer 314 or the second protective layer 315 may be provided. According to driving of the display apparatus using the organic light emitting device of the present invention, display of favorable image quality for a long time can be obtained.

Note that the device is not limited to the switching device, and a monocrystalline silicon substrate, MIM device, a-Si type, or the like can be easily applied to the above display apparatus.

Hereinafter, the present invention is described more specifically by way of examples, but the present invention is not limited thereto.

<Example 1> (Synthesis of Exemplified Compound B-20)

(1) The following regents and solvent were loaded in a 500-ml reactor.

Compound F1: 25 g (113 mmol)

N-bromosuccinyl imide: 24.1 g (135 mmol)

Benzoyl peroxide: 2.74 g

Carbon tetrachloride: 357 ml

Next, the inside of the reactor was made an argon atmosphere, and the reaction solution was then stirred for 2 hours while heated at 80° C. Next, after the reaction solution was cooled, a crystal was deposited by adding isopropyl ether to the solution. The precipitated crystal was filtered, and the resultant crystal was then washed with a little amount of isopropyl ether, and dried, whereby 26.3 g of Compound F2 as a brown crystal was obtained (yield 77%).

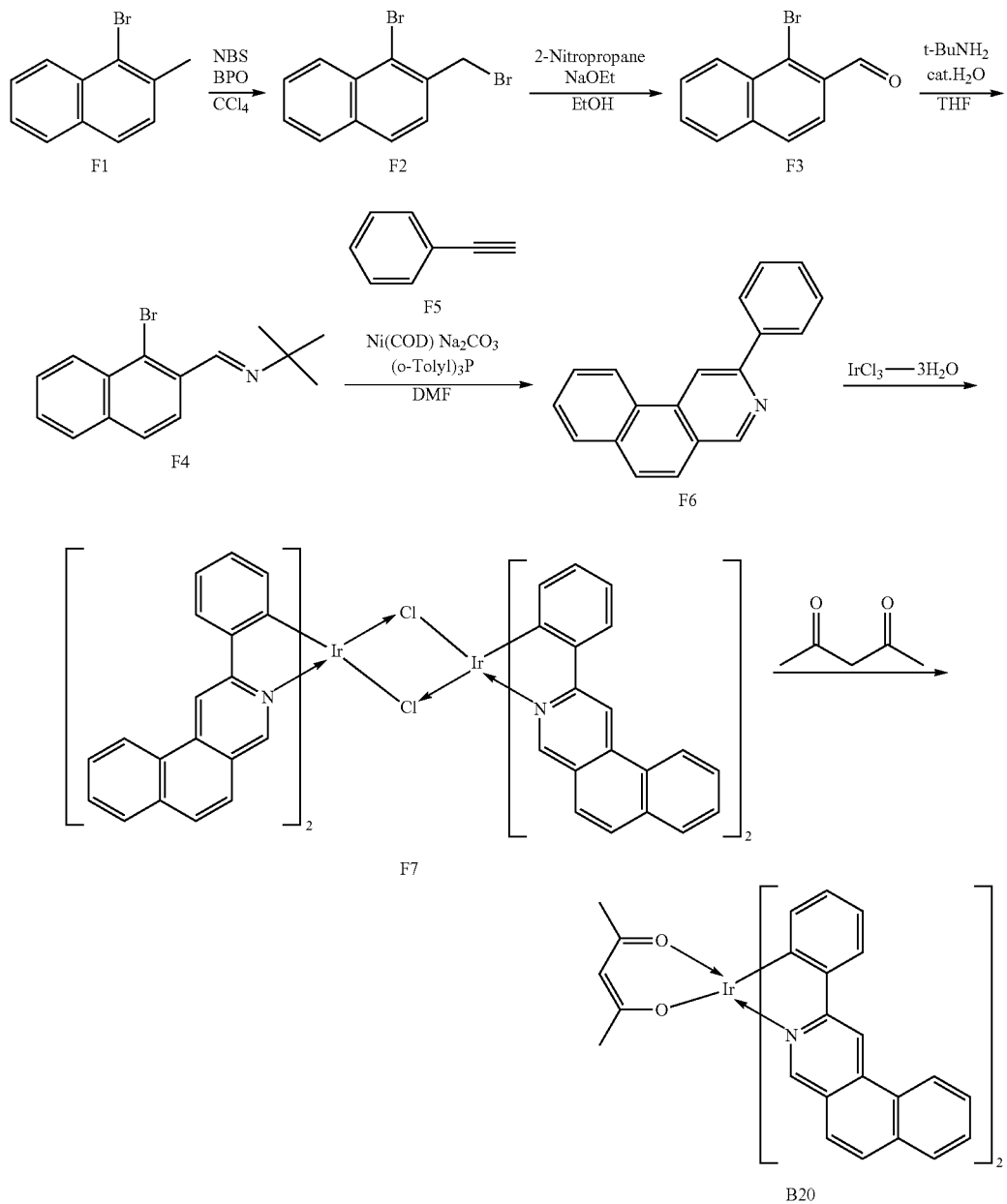

(2) The following regents and solvents were loaded in a 200-ml reactor.
Compound F2: 14 g (46.7 mmol)
2-nitropropane: 4.37 g (49 mmol)
Ethanol: 80 ml Next, the inside of the reactor was made an argon atmosphere, and 15.9 g (46.7 mmol) of 20% sodium ethoxide were added into the reactor. After that, the reaction solution was stirred for 18 hours while heated at 40° C. The reaction solution was cooled, followed by vacuum concentration. Next, the obtained concentrate was subjected to a solvent extraction twice with 100 ml of ethyl acetate, whereby an organic layer was collected. Next, the organic layer was washed with water and a saturated salt solution sequentially, and then dried with magnesium sulfate. Next, the filtrate obtained by filtration of the organic layer was concentrated under vacuum, whereby a brownish-red solid was obtained. The solid was washed with a mixed solution containing isopropyl ether and hexane at 1:1, and then dried, whereby 8.07 g of Compound F3 as a pale brown crystal were obtained (yield 73%).

(3) The following regents and solvent were loaded in a 50-ml reactor.
Compound F3: 8 g (34.0 mmol)
Tetrahydrofuran: 10 ml
tert-butyl amine: 7.47 g Next, 3 ml of distilled water were added to the reaction solution, followed by stirring at room temperature for 24 hours. After the completion of the reaction, the reaction solution was concentrated under vacuum. Next, after 20 ml of water were added to the solution, the obtained solution was subjected to a solvent extraction twice with 50 ml of diethyl ether, whereby an organic layer was collected. Next, the collected organic layer was washed with water once, then washed with a saturated salt solution once, and dried with magnesium sulfate. Next, the obtained filtrate by filtration of the organic layer was concentrated under vacuum, whereby 9.68 g of Compound F4 as a brown solid were obtained (yield 99%).

(4) The following regents and solvent were loaded in a 300-ml reactor.
Bis(1,5-cyclooctadiene)nickel: 0.36 mg (1.31 mmol)
Tris(o-tolyl)phosphine: 0.796 g (2.62 mmol)
Sodium carbonate: 2.77 g (26.2 mmol)
Degassed dimethylformamide: 80 ml Next, the inside of the reactor was made an argon atmosphere, and the reaction solution was then stirred for 30 minutes. After that, the following reagents were further added.
Compound F4: 7.59 g (26.2 mmol)
Phenyl acetylene (Compound F5): 5.34 g (52.3 mmol)

Next, the reaction solution was stirred for 3 hours while heated at 100° C. Next, the reaction solution was cooled and water was added thereto, and then the solution was concentrated under vacuum. Next, the solution was subjected to a solvent extraction three times with 100 ml of a mixture solvent containing isopropyl ether and ethyl acetate at 1:1, whereby an organic layer was collected. The organic layer was washed with water and a saturated salt water sequentially, and then dried with magnesium sulfate. Next, the filtrate obtained by filtration of the organic layer was concentrated under vacuum, whereby a black liquid having viscosity was obtained. The liquid was subjected to column chromatography (developing solvent: chloroform/ethyl acetate=20/1), and then further subjected to column chromatography (developing solvent: hexane/ethyl acetate=5/1) for purifying, whereby a brown solid was obtained. Next, the brown solid was dissolved in a little amount of ethyl acetate, and recrystallized by adding a solution containing isopropyl ether and hexane at 1:1. Next, the crystal obtained by recrystallization was dried, whereby 4.2 g of Compound F6 as a pale brown crystal were obtained (yield 62%).

(5) The following regents and solvent were loaded in a 100-ml three-necked flask.
Iridium (III) trihydrate: 0.658 g (3.74 mmol)
Compound F6: 2.00 g (16 mmol)
Ethoxyethanol: 20 ml
Water: 6 ml Next, the reaction solution was stirred for 30 minutes at room temperature in a stream of nitrogen. Next, the reaction solution was stirred for 10 hours while heated at 80° C. Next, the reaction solution was cooled to room temperature, and the deposited precipitate was filtered and washed with water, followed by washing with ethanol. After the washing, the precipitate was dried under reduced pressure at room temperature, whereby 2.2 g of Compound F7 as a yellowish brown powder were obtained (yield 80%).

(6) The following regents and solvents were loaded in a 100-ml three-necked flask.
Ethoxyethanol: 45 ml
Compound F7: 2.2 g (1.48 mmol)
Acetylacetone: 0.89 g (8.9 mmol)
Sodium carbonate: 0.792 g (7.48 mmol)

Next, the reaction solution was stirred for 1 hour at room temperature in a stream of nitrogen, and then stirred for 8 hours while heated at 120° C. Next, a precipitate was deposited by cooling the reaction solution with ice, and the deposited precipitate was filtered, followed by washing with water. Next, the precipitate was washed with ethanol, dissolved in chloroform, and an insoluble matter was filtered. Next, the obtained filtrate was concentrated, and recrystallized with a chloroform-methanol mixture solvent, whereby 0.42 g of Exemplified Compound B20 as a yellowish brown powder was obtained (yield 35%).

In addition, the structure of the compound was confirmed with an NMR measurement.

$^1$H-NMR (CDCl$_3$, 400 MHz) σ (ppm): 9.22 (s, 2H), 8.99 (s, 2H), 8.85 (d, 2H, J=7.6 Hz), 7.97 (d, 2H, J=8.0 Hz), 7.86 (m, 10H, J=8.8 Hz), 6.88 (t, 2H, J=6.8 Hz), 6.65 (t, 2H, J=6.4 Hz), 6.26 (d, 3H, J=7.6 Hz), 5.27 (s, 1H), 1.84 (s, 6H).

Figure 4:
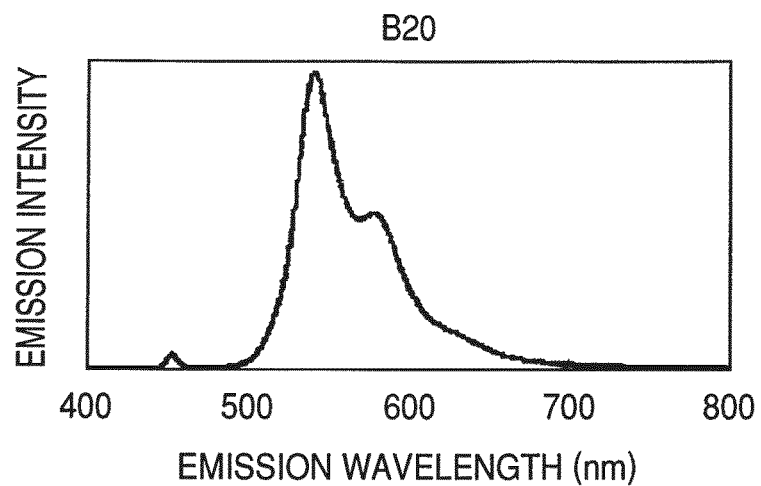
FIG. 4 is a diagram illustrating a PL spectrum of Exemplified Compound B-20 in $1\times10^{-5}$ mol/l toluene solution.

Further, an emission spectrum (PL spectrum) of Exemplified Compound B20 in a 1×10$^{-5}$ mol/l toluene solution was measured using F-4500 manufactured by Hitachi, Ltd. Specifically, photoluminescence (PL) at an excitation wavelength of 450 nm was measured. As a result, a PL spectrum having a maximum peak intensity at 538 nm as illustrated in FIG. 4 was obtained.

On the other hand, a quantum efficiency of Exemplified Compound B20 was calculated from an absorbance and a light emission area of the compound itself. The result is shown in Table 5. Note that the absorbance was evaluated from an absorbent spectrum in a 1×10$^{-5}$ mol/l toluene solution which was measured by using a ultraviolet and visible spectrophotometer V-560 manufactured by JASCO Corporation.

Example 2 (Synthesis of Exemplified Compound B1)

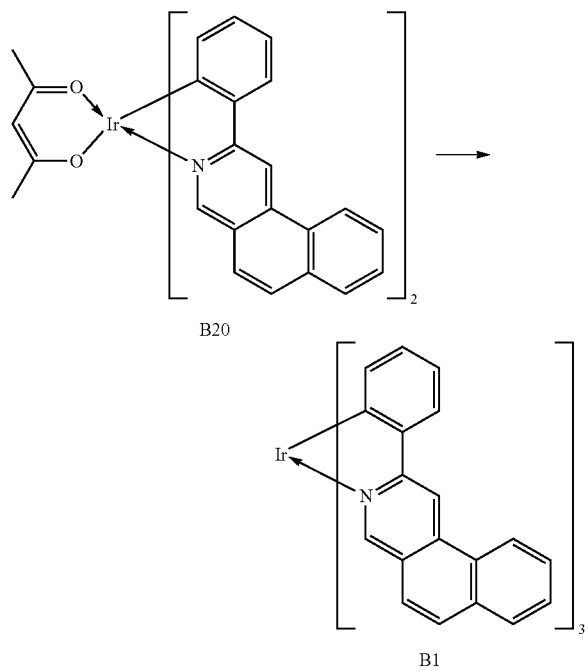

The following regents and solvent were loaded in a 50-ml three-necked flask.
Glycerol: 10 ml
Exemplified Compound B20: 0.5 g (0.625 mmol)
Compound E06: 0.319 g (1.25 mmol)

Next, the reaction solution was stirred for 8 hours in a stream of nitrogen while heated at 200° C. Next, 20 ml of water were added to the reaction solution, followed by further stirring. Then, the deposited precipitate was filtered, and washed with ethanol. The precipitate was filtered with dimethyl formamide upon heating, and thereafter, recrystallized by cooling, whereby 0.301 g of Exemplified Compound B1 as a yellowish brown powder was obtained (yield 50%).

In addition, the structure of the compound was confirmed by an NMR measurement.

$^1$H-NMR (CDCl$_3$, 400 MHz) σ (ppm): 9.08 (s, 3H), 8.81 (d, 3H, J=8.4 Hz), 8.23 (s, 3H), 8.98 (d, 3H, J=7.2 Hz), 7.85 (d, 3H, J=6.4 Hz), 7.73 (m, 9H, J=6.8 Hz), 7.57 (d, 3H, J=8.4 Hz), 7.28 (m, 3H, J=8.4 Hz), 6.99 (t, 3H, J=7.2 Hz), 6.88 (d, 3H, J=7.2 Hz).

Figure 5:
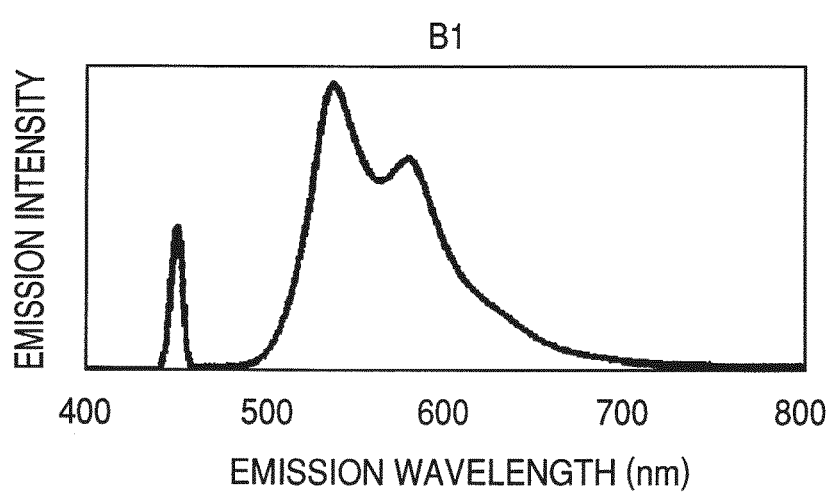
FIG. 5 is a diagram illustrating a PL spectrum of Exemplified Compound B-1 in $1\times10^{-5}$ mol/l toluene solution.

Further, a PL spectrum of Exemplified Compound B1 was measured in a 1×10$^{-5}$ mol/l toluene solution in the same manner as in Example 1 (excitation wavelength: 450 nm). As a result, the PL spectrum having a maximum peak wavelength at 536 nm as illustrated in FIG. 5 was obtained.

On the other hand, the quantum efficiency of Exemplified Compound B1 was calculated in the same manner as in Example 1. Results are shown in Table 5.

Comparative Example 1

Organic Metal Complex K1 shown below was synthesized and the PL spectrum was measured in the same manner as in Example 1. In addition, the quantum efficiency was calculated in the same manner as in Example 1. Results were shown in Table 5.

K1

TABLE 5

|  |  | Maximum peak wavelength (mm) | Quantum efficiency |
|---|---|---|---|
| Example 1 | Exemplified Compound B20 | 538 | 1.3$^{(Remark)}$ |
| Example 2 | Exemplified Compound B1 | 536 | 1.3$^{(Remark)}$ |
| Comparative Example 1 | K1 | 514 | 1.0$^{(Remark)}$ |

$^{(Remark)}$ the quantum efficiency is a relative quantum efficiency when the quantum efficiency of K1 is defined as 1.0.

From Table 5, when the PL spectra of the organic metal complexes in Examples 1 and 2 and Organic Metal Complex K1 were compared, the organic metal complexes in Examples 1 and 2 each had a maximum peak wavelength at a longer wavelength side than that of Organic Metal Complex K1, and difference of the maximum peak wavelength between the complexes in Examples 1 and 2 and Organic Metal Complex K1 was small. This is because an aromatic ring was fused non-linearly with respect to a basic skeleton containing nitrogen which forms a coordinate bond with an iridium atom and lengthening of the emission wavelength could be prevented. In addition, from FIG. 5, it was indicated that the quantum efficiency of the organic metal complexes of Examples 1 and 2 was higher than that of Organic Metal Complex K1. The reason may be as follows. The aromatic ring was fused to the basic skeleton containing nitrogen which forms a coordinate bond with an iridium atom in a direction away from the iridium atom, whereby the oscillator strength of molecules themselves was improved. As a result, the quantum efficiency was improved.

Example 3 (Synthesis of Exemplified Compound A30)

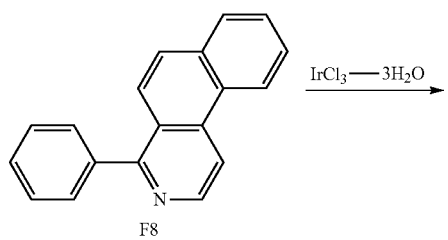

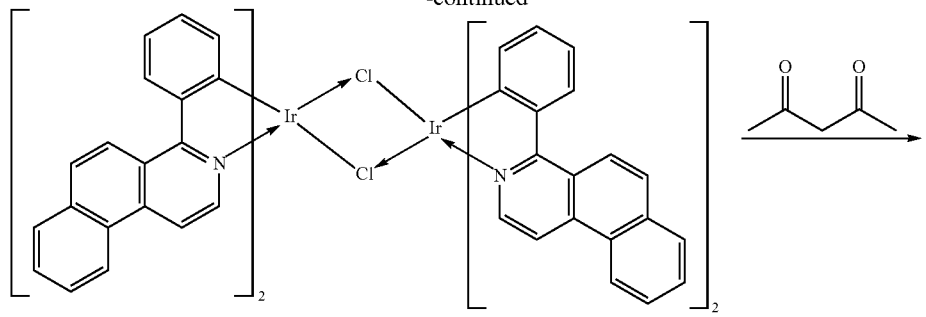

F9

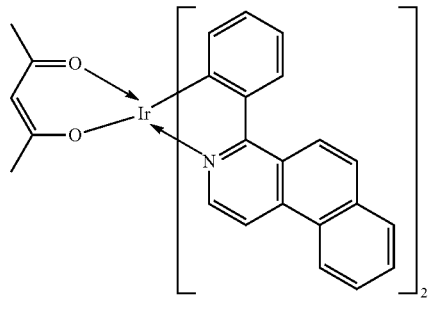

A30

1.5 g (2 mmol) of Exemplified Compound A30 were obtained by a reaction according to the method in Example 1 except that Compound F6 was changed to Compound F8 (3 g, 0.012 mol) in the section (5) of Example 1.

In addition, the structure of Compound A30 was confirmed by an NMR measurement.

$^1$H-NMR (CDCl$_3$, 400 MHz) σ (ppm): 8.86 (d, 2H, J=9.2 Hz), 8.72 (m, 4H, J=6.8 Hz), 8.30 (d, 2H, J=6.4 Hz), 8.18 (d, 2H, J=8.0 Hz), 7.98 (m, 4H, J=9.6 Hz), 7.76 (m, 4H, J=4.0 Hz), 6.91 (t, 2H, J=7.2 Hz), 6.66 (t, 2H, J=7.6 Hz), 6.13 (d, 2H, J=6.4 Hz), 5.23 (s, 1H), 1.78 (s, 6H).

Figure 6:
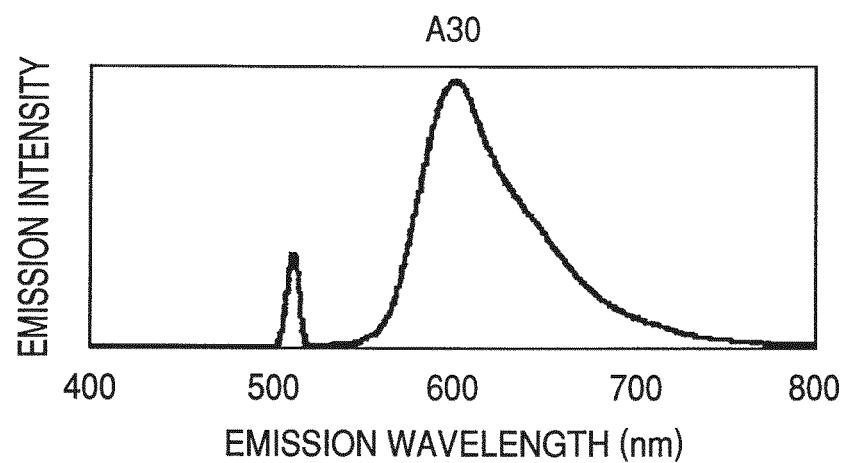
FIG. 6 is a diagram illustrating a PL spectrum of Exemplified Compound A-30 in $1\times10^{-5}$ mol/l toluene solution.

Further, a PL spectrum of Exemplified Compound A30 was measured in a 1×10$^{-5}$ mol/l toluene solution in the same manner as in Example 1 (excitation wavelength: 510 nm). As a result, the PL spectrum having a maximum peak wavelength at 601 nm as illustrated in FIG. 6 was obtained. On the other hand, the quantum efficiency of Exemplified Compound A30 was calculated in the same manner as in Example 1. Results are shown in Table 6.

<Example 4> (Synthesis of Exemplified Compound A1)

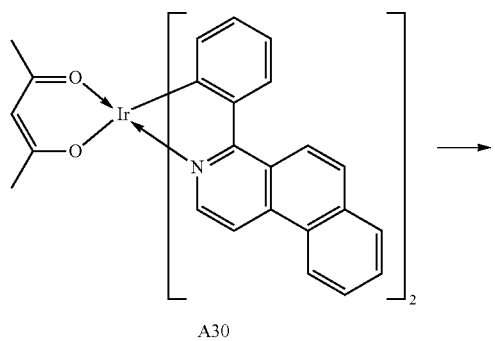

A30

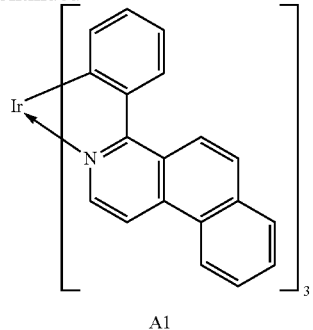

A1

0.2 g (0.2 mol) of Exemplified Compound A1 was obtained by a reaction according to the method in Example 2 except that Exemplified Compound A30 (0.8 g, 1 mmol) instead of Exemplified Compound B20 and Compound F8 (0.63 g, 2.5 mol) instead of Compound F6 were used.

In addition, the structure of Compound A1 was confirmed by an NMR measurement.

$^1$H-NMR (CDCl$_3$, 400 MHz) σ (ppm): 8.85 (d, 3H, J=8.0 Hz), 8.48 (d, 3H, J=8.0 Hz), 8.18 (d, 3H, J=7.6 Hz), 7.92 (m, 9H, J=6.4 Hz), 7.68 (m, 6H, J=6.8 Hz), 7.53 (d, 3H, J=6.4 Hz), 7.07 (d, 3H, J=7.2 Hz), 7.01 (t, 3H, J=7.2 Hz), 6.91 (t, 3H, J=7.2 Hz).

Figure 7:
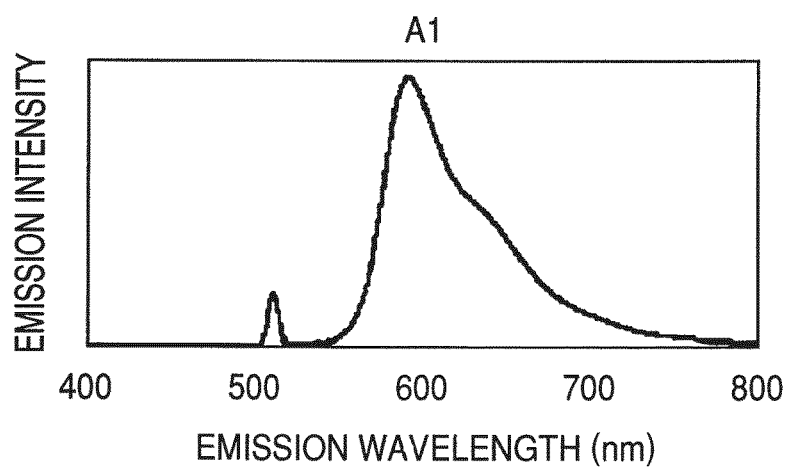
FIG. 7 is a diagram illustrating a PL spectrum of Exemplified Compound A-1 in $1\times10^{-5}$ mol/l toluene solution.

Further, a PL spectrum of Exemplified Compound B1 was measured in a 1×10$^{-5}$ mol/l toluene solution in the same manner as in Example 1 (excitation wavelength: 510 nm). As a result, the PL spectrum having a maximum peak wavelength at 592 nm as illustrated in FIG. 7 was obtained. On the other hand, the quantum efficiency of Exemplified Compound A1 was calculated in the same manner as in Example 3. Results are shown in Table 6.

Comparative Example 2

Organic Metal Complex K2 shown below was synthesized, whereby a PL spectrum was measured in the same manner as in Example 1. In addition, a quantum efficiency was calculated in the same manner as in Example 3. Results were shown in Table 6.

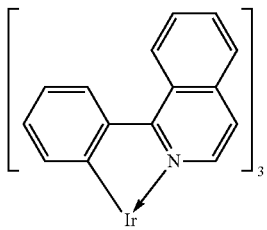

K2

TABLE 6

| | | Maximum peak wavelength (mm) | Quantum efficiency |
|---|---|---|---|
| Example 3 | Exemplified Compound A30 | 601 | 1.6(Remark) |
| Example 4 | Exemplified Compound A1 | 592 | 1.6(Remark) |
| Comparative Example 1 | K2 | 619 | 1.0(Remark) |

(Remark)the quantum efficiency is a relative quantum efficiency when the quantum efficiency of K2 is defined as 1.0.

From Table 6, when the PL spectra of the organic metal complexes in Examples 3 and 4 and Organic Metal Complex K2 were compared, the organic metal complexes in Examples 3 and 4 each had a maximum peak wavelength at a shorter wavelength side than that of Organic Metal Complex K2. This is because an aromatic ring was fused non-linearly with respect to a basic skeleton containing nitrogen which forms a coordinate bond with an iridium atom and lengthening of the emitting light wavelength could be prevented. In addition, from Table 6, it was indicated that the quantum efficiency of the organic metal complexes of Examples 3 and 4 was higher than that of Organic Metal Complex K2. The reason may be as follows. The aromatic ring was fused to a basic skeleton containing nitrogen which forms a coordinate bond with an iridium atom in a direction away from the iridium atom, whereby the oscillator strength of molecules themselves was improved. As a result, the quantum efficiency was improved.

Example 5

An organic light emitting device in which an anode, a hole transport layer, an emission layer, an electron transport layer, and a cathode were provided on a substrate sequentially was produced.

First, an ITO was patterned on a glass substrate to form an anode. At this time, a film thickness of the anode was set to 100 nm, and an electrode area was set to 3 mm².

Next, in a vacuum chamber at $10^{-5}$ Pa, the following organic compound layer and electrode layer were continuously formed into a film on the anode by vacuum deposition with resistance heating. Specifically, H-1 shown below was deposited to form a hole transport layer. At this time, a film thickness of the hole transport layer was set to 20 nm. Next, H-2 shown below as a host and Exemplified Compound A1 as a guest were co-deposited so that an amount of the guest became 5 wt % with respect to the host, whereby an emission layer was formed. In this time, a film thickness of the emission layer was set to 30 nm. Then, H-3 below was deposited to form an electron transport layer. In this time, a film thickness of the electron transport layer was set to 30 nm. Next, KF was deposited to form a first metal electrode layer. In this time, a film thickness of the first metal electrode layer was set to 1 nm. Next, Al was deposited, whereby a second metal electrode was formed. In this time, a film thickness of the second metal electrode layer was set to 100 nm. Note that the first metal electrode layer and the second metal electrode layer each function as a cathode. As described above, the organic light emitting device was obtained.

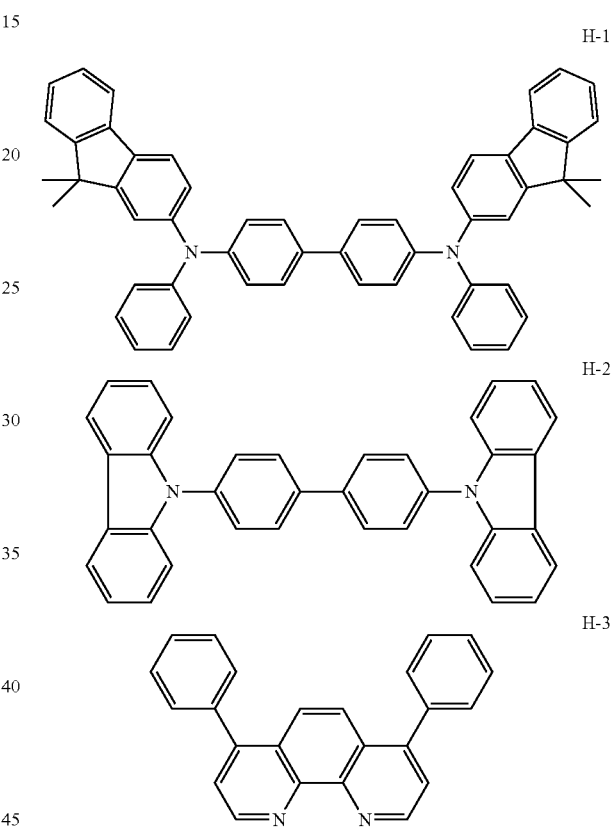

A current-voltage characteristic of the obtained device was measured using a minute current ammeter 4140B manufactured by Hewlett-Packard Development Company, L.P. In addition, emission characteristics of the obtained device were measured with BM7 manufactured by TOPCON CORPORATION. Note that when respective characteristics were measured, an emission luminance was set to 1,000 cd/m². Measured results are shown in Table 7.

Example 6

An organic light emitting device was formed in the same manner as in Example 5 except that an emission layer was formed by co-deposition so that an amount of a guest was 15 wt % with respect to a host. In addition, emission characteristics of the obtained device were measured in the same manner as in Example 5. Results are shown in Table 7.

Example 7

An organic light emitting device was formed in the same manner as in Example 5 except that Exemplified Compound A1 as a guest was changed to Exemplified Compound B1. In addition, emission characteristics of the obtained device were measured in the same manner as in Example 5. Results are shown in Table 7.

TABLE 7

| | Emission wavelength (nm) | Light emitting efficiency (cd/A) | Voltage (V) |
|---|---|---|---|
| Example 5 | 595 | 25 | 3.5 |
| Example 6 | 610 | 17 | 3.4 |
| Example 7 | 535 | 50 | 4.0 |

What is claimed is:

1. An organic metal complex having a structure represented by the following general formula (1):

$$ML_mL'_n \quad (1)$$

where:

M represents a metal atom selected from Ir, Pt, Rh, Os, and Zn;

L and L', which are different from each other, each represent a bidentate ligand;

m represents an integer of 1 to 3 and n represents an integer of 0 to 2, provided that m+n is 3;

a partial structure $ML_m$ represents a structure represented by the following general formula (2):

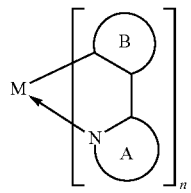

(2)

where:

A represents a structure represented by the following general formula (3), which has, as a basic skeleton, a benzo[f]isoquinoline ring:

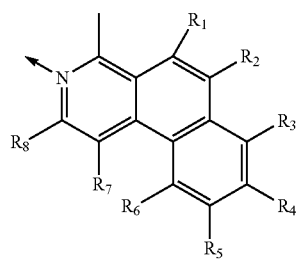

(3)

where:

$R_1$ to $R_8$, which may be identical to or different from each other, each represent a hydrogen atom, a halogen atom, a substituted or unsubstituted alkyl group, an alkoxy group, an aralkyl group, a substituted amino group, a substituted or unsubstituted aryl group, or a substituted or unsubstituted heterocyclic group, and adjacent substituents among $R_1$ to $R_8$ may be bonded to form a ring; and B represents a fused ring which may have a substituent and the fused ring is a naphthalene ring; and a partial structure $ML'_n$ represents a structure including a monovalent bidentate ligand; provided that:

i) at least one of $R_1$ to $R_8$ is not a hydrogen atom, ii) B represents a fused ring which has a substituent not being a hydrogen atom, or iii) at least one of $R_1$ to $R_8$ is not a hydrogen atom and B represents a fused ring, which has a substituent not being a hydrogen atom.

2. The organic metal complex according to claim 1, wherein:

the partial structure $ML_m$ has a structure represented by the following general formula (8):

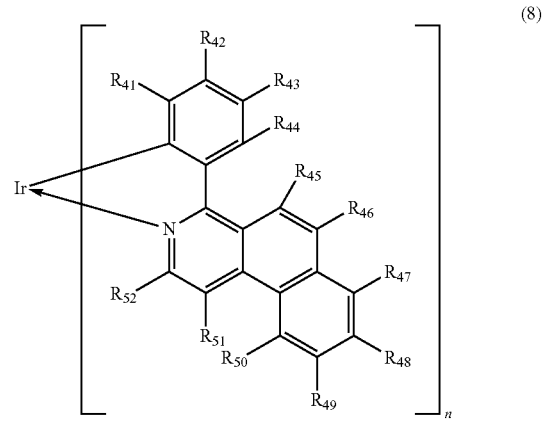

(8)

wherein, of those substituents represented by $R_{41}$ to $R_{44}$, adjacent substituents are bonded to form a naphthalene ring; wherein $R_{41}$ to $R_{52}$ each represents a hydrogen atom, halogen atom, a substituted or unsubstituted alkyl group, an alkoxy group, an aralkyl group, an amino group, a substituted or unsubstituted aryl group, or a substituted or unsubstituted heterocyclic group;

provided that i) at least one of $R_{45}$ to $R_{52}$ is not a hydrogen atom, ii) the naphthalene ring has a substituent not being a hydrogen atom, or iii) at least one of $R_{45}$ to $R_{52}$ is not a hydrogen atom and the naphthalene ring has a substituent not being a hydrogen atom.

3. The organic metal complex according to claim 1, wherein:

M represents Ir; and the partial structure $ML'_n$ has a structure represented by any one of the following general formulae (10) to (12):

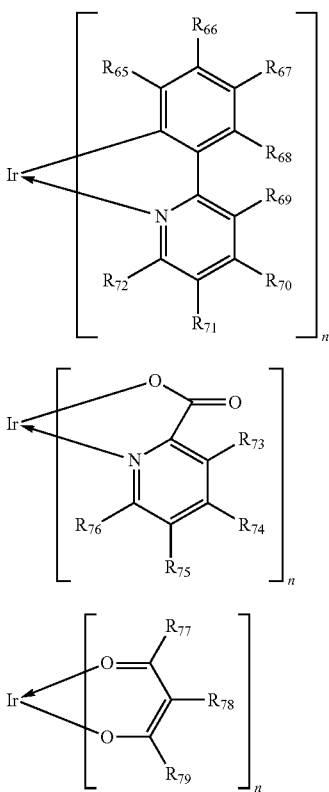

(10)

(11)

(12)

where $R_{65}$ to $R_{79}$, which may be identical to or different from each other, each represent a hydrogen atom, a halogen atom, a substituted or unsubstituted alkyl group, an alkoxy group, an aralkyl group, a substituted amino group, a substituted or unsubstituted aryl group, or a substituted or unsubstituted heterocyclic group, and adjacent substituents among $R_{65}$ to $R_{72}$, among $R_{73}$ to $R_{76}$, or among $R_{77}$ to $R_{79}$ may be bonded to form a ring.

4. The organic metal complex according to claim 1, wherein $R_3$ and $R_4$ may be bonded to form a benzene ring that is fused with the benzo[f]isoquinoline ring represented in the formula (3).

5. The organic metal complex according to claim 2, wherein $R_{47}$ and $R_{48}$ may be bonded to form a benzene ring that is fused with the benzo[f]isoquinoline ring represented in the formula (8).

6. The organic metal complex according to claim 3, wherein adjacent substituents among $R_{65}$ to $R_{68}$, may be bonded to form a ring that is fused with the benzene ring represented in the formula (10).

7. The organic metal complex according to claim 3, wherein adjacent substituents among $R_{77}$ to $R_{79}$ may be bonded to form a ring that is fused with a backbone represented in the formula (12).

8. An organic light emitting device, comprising:
an anode;
a cathode; and
a layer formed of an organic compound, which is sandwiched between the anode and the cathode,
wherein the layer formed of an organic compound comprises the organic metal complex according to claim 1.

9. The organic light emitting device according to claim 8, wherein the organic metal complex is incorporated in an emission layer.

10. The organic light emitting device according to claim 9, wherein the emission layer comprises a host material and another material which is different from the host material, and the another material is the organic metal complex.

11. The organic light emitting device according to claim 10, wherein the weight ratio of the organic metal complex is 0.01 to 20 wt % with respect to the host material.

12. The organic light emitting device according to claim 8, wherein the organic light emitting device emits a red light.

13. An apparatus comprising the organic light emitting device according to claim 8; and a substrate.

14. The apparatus according to claim 13, wherein the organic light emitting device being provided on the substrate,
wherein the apparatus has a bottom emission structure in which the light which the organic light emitting device emits is extracted from the substrate side.

15. The apparatus according to claim 14, wherein the organic light emitting device being provided on the substrate,
wherein the apparatus has a top emission structure in which the light which the organic light emitting device emits is extracted from a side opposite to the substrate.

16. A luminescent ink comprising a solvent and the organic metal complex according to claim 1.

* * * * *